US012637457B2

(12) United States Patent
Cheng et al.

(10) Patent No.: US 12,637,457 B2
(45) Date of Patent: May 26, 2026

(54) SALT FORM AND CRYSTAL FORM OF JAK INHIBITOR, PREPARATION METHOD THEREFOR, AND USE THEREOF

(71) Applicant: SHANGHAI FUDAN-ZHANGJIANG BIO-PHARMACEUTICAL CO., LTD., Shanghai (CN)

(72) Inventors: Ming Cheng, Shanghai (CN); Yaqi Cao, Shanghai (CN); Junen Sun, Shanghai (CN); Yu Pu, Shanghai (CN); Jianping Jiang, Shanghai (CN); Wenbo Zhang, Shanghai (CN)

(73) Assignee: Shanghai Fudan-Zhangjiang Bio-Pharmaceutical Co., Ltd., Shanghai (CN)

( * ) Notice: Subject to any disclaimer, the term of this patent is extended or adjusted under 35 U.S.C. 154(b) by 593 days.

(21) Appl. No.: 18/021,032

(22) PCT Filed: Aug. 12, 2021

(86) PCT No.: PCT/CN2021/112278

§ 371 (c)(1),
(2) Date: Feb. 13, 2023

(87) PCT Pub. No.: WO2022/033551

PCT Pub. Date: Feb. 17, 2022

(65) Prior Publication Data

US 2023/0295160 A1 Sep. 21, 2023

(30) Foreign Application Priority Data

Aug. 14, 2020 (WO) ................ PCT/CN2020/109279
Feb. 3, 2021 (WO) ................ PCT/CN2021/075086

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

U.S. PATENT DOCUMENTS

2018/0002328 A1 1/2018 Li et al.

FOREIGN PATENT DOCUMENTS

| | | |
|---|---|---|
| CN | 107428749 A | 12/2017 |
| WO | 2014164409 A1 | 10/2014 |
| WO | 2016119700 A1 | 8/2016 |

OTHER PUBLICATIONS

Apr. 25, 2024 the First Office Action issued in Chinese Patent Application No. 202180061258.0.

Apr. 23, 2024 Search Report issued in Chinese Patent Application No. 202180061258.0.

Notice of Reasons of Refusal issued in Japanese Patent Application No. 2023-507518, mailed Jan. 21, 2025.

International Search Report issued in International Patent Application No. PCT/CN2021/112278, mailed Nov. 17, 2021.

Written Opinion of the International Searching Authority issued in International Patent Application No. PCT/CN2021/112278, mailed Nov. 17, 2021.

Oct. 24, 2024, the Second Office Action issued in Chinese Patent Application No. 2021800612580.

Oct. 21, 2024, the Supplementary Search Report issued in Chinese Patent Application No. 2021800612580.

Sep. 17, 2024, the extended European search report issued in European Patent Application No. 21855601.7.

Bastin R J et al: "Salt Selection and Optimization for Pharmaceutical New Chemical Entities", Organic Process Research and Development, Cambridge, GB, vol. 4, No. 5, pp. 427-435, Jan. 1, 2000. DOI: 10.1021/op000018u.

Decision of Refusal issued in Japanese Patent Application No. 2023-507518, mailed Aug. 5, 2025.

*Primary Examiner* — Kamal A Saeed
*Assistant Examiner* — Quincy McKoy
(74) *Attorney, Agent, or Firm* — Pilloff Passino & Cosenza LLP; Rachel Pilloff; Sean Passino

(57) ABSTRACT

Provided in the present invention are a salt form and a crystal form of a JAK inhibitor, a preparation method therefor, and the use thereof. An X-ray powder diffraction pattern of a crystal form A of a compound as shown in formula I has characteristic diffraction peaks at the 2θ angles of 5.9°±0.2°, 7.4°±0.2°, 11.6°±0.2°, 21.7°±0.2° and 23.8°±0.2°.

I

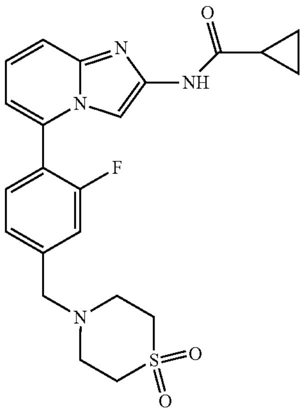

20 Claims, 8 Drawing Sheets

SALT FORM AND CRYSTAL FORM OF JAK INHIBITOR, PREPARATION METHOD THEREFOR, AND USE THEREOF

The present application claims priorities of PCT patent application PCT/CN2020/109279 with a filing date of Aug. 14, 2020 and PCT patent application PCT/CN2021/075086 with a filing date of Feb. 3, 2021. The contents of the patent applications are incorporated herein by reference in their entireties.

TECHNICAL FIELD

The present disclosure relates to a salt form and a crystal form of a JAK inhibitor, a preparation method therefor, and a use thereof.

BACKGROUND

Janus kinase (JAK) signaling pathway found in interferon-induced receptor-mediated gene expression has been shown to be a common signaling pathway used by many cytokines and growth factors. The mammalian JAK family of intracellular tyrosine kinases has four members: Janus kinase 1 (JAK1), Janus kinase 2 (JAK2), Janus kinase 3 (JAK3), and tyrosine kinase 2 (TYK2). JAK ranges in size from 120 to 140 kDa and contains seven conserved JAK homology (JH) domains that define this kinase superfamily.

Each JAK isoform may be used by multiple cytokine pathways, and even the biological activity of many cytokines may be inhibited and regulated by single or multiple JAKs. Inhibition of JAKs can be used to prevent, inhibit or treat the evolution or attack of various diseases and disorders, including hyperproliferative diseases and cancers such as leukemias and lymphomas, immune and inflammatory disorders such as transplant rejection, asthma, chronic obstructive pulmonary disease, allergy, rheumatoid arthritis, psoriasis, atopic dermatitis, Crohn's disease, ulcerative colitis, amyotrophic lateral sclerosis and multiple sclerosis.

WO2016119700A1 discloses that the compound shown in formula I is an effective JAK inhibitor for preventing or treating one or more symptoms of Janus kinase-mediated diseases;

I

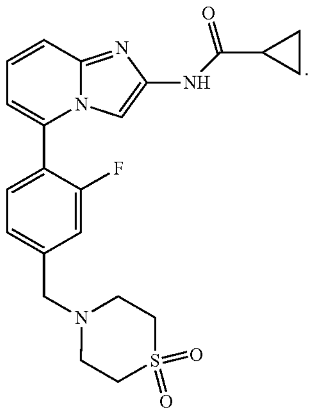

The solubility of the free base form of the compound shown in formula I in water is too low, which may affect its dissolution and absorption in vivo, resulting in too low bioavailability, making it unsuitable for further drug development. At the same time, because the water solubility is too low, it is not easy to be purified in the production process, which brings certain difficulties to industrial production.

CONTENT OF THE PRESENT INVENTION

The present disclosure provides a salt form and a crystal form of a JAK inhibitor, a preparation method therefor, and a use thereof. The salt form and the crystal form have good JAK kinase inhibitory activity, solubility, stability and bioavailability, which enhance the developability of the oral preparation of the compound shown in formula I.

The present disclosure provides a crystal form A of a hydrochloride hydrate of a compound shown in formula I, and an X-ray powder diffraction (XRPD) pattern thereof has characteristic diffraction peaks at the following 2θ angles: 5.9°±0.2°, 7.4°±0.2°, 11.6°±0.2°, 21.7°±0.2° and 23.8°±0.2°;

I

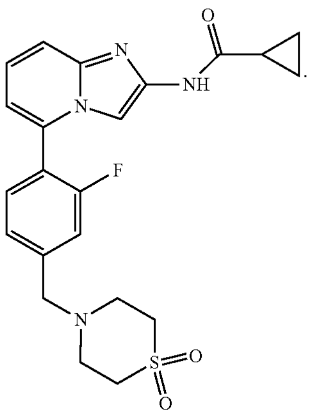

In some embodiments of the present disclosure, the X-ray powder diffraction pattern of the crystal form A has characteristic diffraction peaks at the following 2θ angles: 5.9°±0.2°, 7.4°±0.2°, 11.6°±0.2°, 17.7°±0.2°, 17.8°±0.2°, 21.7°±0.2°, 23.6°±0.2°, 23.8°±0.2°, 29.0°±0.2°, 30.4°±0.2° and 34.9°±0.2°.

In some embodiments of the present disclosure, the X-ray powder diffraction pattern of the crystal form A has characteristic diffraction peaks at the following 2θ angles: 5.9°±0.2°, 7.4°±0.2°, 8.9°±0.2°, 11.6°±0.2°, 14.6°±0.2°, 17.7°±0.2°, 17.8°±0.2°, 18.7°±0.2°, 19.5°±0.2°, 21.0°±0.2°, 21.7°±0.2°, 21.9°±0.2°, 22.6°±0.2°, 23.6°±0.2°, 23.8°±0.2°, 29.0°±0.2°, 30.4°±0.2°, 33.3°±0.2°, 34.9°±0.2° and 37.7°±0.2°.

In some embodiments of the present disclosure, the X-ray powder diffraction pattern of the crystal form A has characteristic diffraction peaks at the following 2θ angles: 5.9°±0.2°, 6.6°±0.2°, 7.4°±0.2°, 8.9°±0.2°, 10.5°±0.2°, 11.6°±0.2°, 12.3°±0.2°, 13.9°±0.2°, 14.2°±0.2°, 14.6°±0.2°, 17.1°±0.2°, 17.7°±0.2°, 17.8°±0.2°, 18.7°±0.2°, 19.5°±0.2°, 20.4°±0.2°, 21.0°±0.2°, 21.2°±0.2°, 21.7°±0.2°, 21.9°±0.2°, 22.6°±0.2°, 23.6°±0.2°, 23.8°±0.2°, 24.9°±0.2°, 26.6°±0.2°, 26.8°±0.2°, 28.3°±0.2°, 29.0°±0.2°, 30.4°±0.2°, 31.2°±0.2°, 32.3°±0.2°, 33.3°±0.2°, 34.2°±0.2°, 34.9°±0.2°, 35.6°±0.2°, 35.9°±0.2°, 36.4°±0.2°, 36.9°±0.2°, 37.7°±0.2°, 39.3°±0.2° and 39.8°±0.2°.

In some embodiments of the present disclosure, the X-ray powder diffraction pattern of the crystal form A has characteristic diffraction peaks at the following 2θ angles: 5.9°, 6.6°, 7.4°, 8.9°, 10.5°, 11.6°, 12.3°, 13.9°, 14.2°, 14.6°, 17.1°, 17.7°, 17.8°, 18.7°, 19.5°, 20.4°, 21.0°, 21.2°, 21.7°, 21.9°, 22.6°, 23.6°, 23.8°, 24.9°, 26.6°, 26.8°, 28.3°, 29.0°, 30.4°, 31.2°, 32.3°, 33.3°, 34.2°, 34.9°, 35.6°, 35.9°, 36.4°, 36.9°, 37.7°, 39.3° and 39.8°.

In some embodiments of the present disclosure, the analytical data of the XRPD pattern of the crystal form A are shown in Table 1.

TABLE 1

Analytical data of the X-ray powder diffraction pattern of the crystal form A

| Diffraction angle (°2θ) | Relative intensity [%] | Diffraction angle (°2θ) | Relative intensity [%] |
|---|---|---|---|
| 5.9 | 20.7 | 23.6 | 15.3 |
| 6.6 | 0.9 | 23.8 | 29.8 |
| 7.4 | 55.4 | 24.9 | 14.3 |
| 8.9 | 7.8 | 26.6 | 1.2 |
| 10.5 | 1.3 | 26.8 | 3.9 |
| 11.6 | 100 | 28.3 | 4.2 |
| 12.3 | 0.7 | 29.0 | 19.0 |
| 13.9 | 3.6 | 30.4 | 19.7 |
| 14.2 | 2.0 | 31.2 | 0.8 |
| 14.6 | 6.2 | 32.3 | 1.2 |
| 17.1 | 3.9 | 33.3 | 8.0 |
| 17.7 | 17.0 | 34.2 | 1.7 |
| 17.8 | 18.8 | 34.9 | 15.6 |
| 18.7 | 5.0 | 35.6 | 3.1 |
| 19.5 | 14.8 | 35.9 | 2.3 |
| 20.4 | 1.7 | 36.4 | 0.8 |
| 21.0 | 9.4 | 36.9 | 0.9 |
| 21.2 | 2.6 | 37.7 | 5.7 |
| 21.7 | 33.6 | 39.3 | 1.0 |
| 21.9 | 11.8 | 39.8 | 2.5 |
| 22.6 | 5.3 | | |

In some embodiments of the present disclosure, the XRPD pattern of the crystal form A is shown in FIG. 1.

In some embodiments of the present disclosure, a thermogravimetric analysis curve of the crystal form A has a weight loss of 8.31±0.50% before 148° C.; and a weight loss of 4.76±0.50% at 148° C. to 228° C.

In some embodiments of the present disclosure, the thermogravimetric analysis curve of the crystal form A has a weight loss of 8.31% before 148° C.; and a weight loss of 4.76% at 148° C. to 228° C.

In some embodiments of the present disclosure, the thermogravimetric analysis curve of the crystal form A has a weight loss of 8.3143% before 148° C.; and a weight loss of 4.7637% at 148° C. to 228° C.

In some embodiments of the present disclosure, the thermogravimetric analysis curve of the crystal form A is shown in FIG. 3.

In some embodiments of the present disclosure, the thermogravimetric analysis curve is detected under the condition that the heating range is 10° C. to 300° C. and the heating rate is 10° C./min.

In some embodiments of the present disclosure, a differential scanning calorimetry (DSC) analysis pattern of the crystal form A has absorption peaks at 165° C.±3° C. and 198° C.±3° C., respectively.

In some embodiments of the present disclosure, the differential scanning calorimetry analysis pattern of the crystal form A has absorption peaks at 165.14° C. and 197.70° C., respectively.

In some embodiments of the present disclosure, the differential scanning calorimetry analysis pattern of the crystal form A has absorption peaks with initial temperatures of 141° C.±3° C. and 179° C.±3° C., respectively.

In some embodiments of the present disclosure, the differential scanning calorimetry analysis pattern of the crystal form A has absorption peaks with initial temperatures of 140.82° C. and 179.20° C., respectively.

In some embodiments of the present disclosure, the differential scanning calorimetry analysis pattern of the crystal form A is shown in FIG. 2.

In some embodiments of the present disclosure, the differential scanning calorimetry analysis pattern is detected under the condition that the heating range is 25° C. to 300° C. and the heating rate is 10° C./min.

In some embodiments of the present disclosure, the crystal form A is a single crystal.

In some embodiments of the present disclosure, the single crystal of crystal form A belongs to a monoclinic crystal system, P21/c space group.

In some embodiments of the present disclosure, the unit cell parameters of the crystal form A are a=15.7298(4) Å, b=19.9360(6) Å, c=8.4652(3) Å, α=90°, β=101.262(3)°, γ=90°.

In some embodiments of the present disclosure, the unit cell volume of the crystal form A is V=2603.47(12) Å3.

The unit cell parameters and/or unit cell volume of the single crystal of the crystal form A can be obtained by X-ray single crystal diffraction detection. The X-ray wavelength λ of the X-ray single crystal diffraction may be 1.54184 Å.

In some embodiments of the present disclosure, in the crystal form A, the compound shown in formula I, HCl and water have a molar ratio of 1:x:y, wherein x is greater than 0 but not greater than 3, and y is greater than 0 but not greater than 3.

In some embodiments of the present disclosure, in the crystal form A, the compound shown in formula I, HCl and water have a molar ratio of 1:2:2.

The present disclosure also provides a preparation method for the crystal form A of the hydrochloride hydrate of the compound shown in formula I, comprising the following steps: precipitating a crystal from a hydrochloride solution of the compound shown in formula I, the crystal being crystal form A; wherein the hydrochloride solution of the compound shown in formula I contains hydrochloride of the compound shown in formula I, an organic solvent and water, and the organic solvent is one or a mixture of two or more selected from methanol, ethanol, n-propanol, n-butanol, isopropanol, isobutanol and tert-butanol. Two or more here should be understood as including two. It should be clear to those skilled in the art that the hydrochloride solution of the compound shown in formula I does not contain other organic solvents, except for unavoidable impurities or solvent residues.

Herein, in the hydrochloride of the compound shown in formula I, the compound shown in formula I and HCl have a molar ratio of 1:x, x being greater than 0 but not greater than 3, for example, 1:2.

In some embodiments, the organic solvent is ethanol.

In some embodiments, the organic solvent and water have a volume ratio of 5-15:0.5-1.5, for example, 10:1 to 6:1, for another example, 10:1 to 8:1, and for still another example, 9:1.

In some embodiments, the temperature of the hydrochloride solution of the compound shown in formula I is 30 to 70° C.

In some embodiments, the step of precipitating the crystal from the hydrochloride solution of the compound shown in formula I comprises: cooling the hydrochloride solution of the compound shown in formula I, for example, the cooling is cooling to 20° C. to 30° C.

In some embodiments, the step of precipitating the crystal from the hydrochloride solution of the compound shown in formula I comprises: stirring the hydrochloride solution of the compound shown in formula I at 20° C. to 30° C. to precipitate the crystal; the stirring time is, for example, 48-96 hours, and for another example, 48 hours.

In some embodiments, the preparation method further comprises: after precipitating the crystal from the hydrochloride solution of the compound shown in formula I, filtering, washing and drying the resulting filter cake to obtain crystal form A.

In some embodiments, the preparation method further comprises: cooling a solution of the crystal form A of the hydrochloride hydrate of the compound shown in formula I for crystallization to obtain a single crystal of the crystal form A of the hydrochloride hydrate of the compound shown in formula I, wherein the solvent of the solution of the crystal form A of the hydrochloride hydrate of the compound shown in formula I is a mixture of ethanol and water; for example, the solution of the crystal form A of the hydrochloride hydrate of the compound shown in formula I has a temperature of 55 to 75° C., for example, 60 to 70° C., for another example, 64 to 66° C.; for example, the mixture of ethanol and water has a volume ratio of ethanol to water of 5-15:0.5-1.5, for example, 10:1 to 6:1, for another example, 10:1 to 8:1, for still another example, 9:1; for example, the cooling is cooling to 20° C. to 30° C.

In some embodiments, the hydrochloride solution of the compound shown in formula I is obtained by mixing a raw material comprising the hydrochloride hydrate of the compound shown in formula I, the organic solvent and water; for example, the hydrochloride solution of the compound shown in formula I is a mixture of the hydrochloride hydrate of the compound shown in formula I, the organic solvent and water. For example, the organic solvent and water have a volume ratio of 5-15:0.5-1.5, for another example, 10:1 to 6:1, for still another example, 10:1 to 8:1, and for yet another example, 9:1; for example, the hydrochloride hydrate of the compound shown in formula I and water have an amount ratio of 250-450 mg:1 mL, for another example, 300-400 mg:1 mL, and for still another example, 350 mg:1 mL.

In some embodiments, the hydrochloride solution of the compound shown in formula I is obtained by mixing a raw material comprising the compound shown in formula I, the organic solvent, water and a concentrated hydrochloric acid solution. For example, the hydrochloride solution of the compound shown in formula I is a mixture of the compound shown in formula I, the organic solvent, water and the concentrated hydrochloric acid solution. For example, the preparation method further comprises: mixing the compound shown in formula I, the organic solvent and water, heating the resulting mixture to 30 to 70° C., adding the concentrated hydrochloric acid solution to obtain the hydrochloride solution of the compound shown in formula I.

Herein, the concentrated hydrochloric acid solution and the compound shown in formula I may have a ratio of, for example, 0.38 mL-0.57 mL:1 g, for example, 0.4 mL-0.5 mL:1 g, for another example, 0.38 mL-0.40 mL:1 g, 0.40 mL-0.42 mL:1 g, 0.42 mL-0.44 mL:1 g, 0.44 mL-0.46 mL:1 g, 0.46 mL-0.48 mL:1 g, 0.48 mL-0.50 mL:1 g, 0.50 mL-0.52 mL:1 g, 0.52 mL-0.54 mL:1 g or 0.54 mL-0.57 mL:1 g.

Herein, the organic solvent and the compound shown in formula I may have a ratio of, for example, 5 mL-15 mL:1 g, for example, 8 mL-12 mL:1 g, for another example, 5 mL-6 mL:1 g, 6 mL-7 mL:1 g, 7 mL-8 mL:1 g, 8 mL-9 mL:1 g, 9 mL-10 mL:1 g, 10 mL-11 mL:1 g, 11 mL-12 mL:1 g, 12 mL-13 mL:1 g, 13 mL-14 mL:1 g, or 14 mL-15 mL:1 g.

Herein, the organic solvent and water may have a volume ratio of, for example, 5-15:0.5-1.5, for another example, 10:1 to 6:1, for still another example, 10:1 to 8:1, and for yet another example, 9:1.

Herein, the water and the compound shown in formula I may have a ratio of, for example, 0.5 mL-1.5 mL:1 g; for example, 0.8 mL-1.2 mL:1 g, and for another example, 0.5 mL-0.6 mL:1 g, 0.6 mL-0.7 mL:1 g, 0.7 mL-0.8 mL:1 g, 0.8 mL-0.9 mL:1 g, 0.9 mL-1.0 mL:1 g, 1.0 mL-1.1 mL:1 g, 1.1 mL-1.2 mL:1 g, 1.2 mL-1.3 mL:1 g, 1.3 mL-1.4 mL:1 g or 1.4 mL-1.5 mL:1 g.

Herein, the organic solvent, water and the compound shown in formula I may have a ratio of, for example, 5 mL-15 mL:0.5 mL-1.5 mL:1 g, for another example, 8 mL-12 mL:0.8 mL-1.2 mL:1 g, and for still another example, 9 mL:1 mL:1 g.

Herein, the organic solvent, water, the concentrated hydrochloric acid solution and the compound shown in formula I may have a ratio of, for example, 5 mL-15 mL:0.5 mL-1.5 mL:0.38 mL-0.57 mL:1 g, for another example, 8 mL-12 mL:0.8 mL-1.2 mL:0.38 mL-0.48 mL:1 g, and for still another example, 9 mL:1 mL:0.41 mL:1 g.

Herein, the concentrated hydrochloric acid solution may have a concentration of, for example, 8 mol/L-12 mol/L, for another example, 10 mol/L-12 mol/L, and for still another example, 12 mol/L.

Herein, in the hydrochloride solution of the compound shown in formula I, HCl and the compound shown in formula I may have a molar ratio of, for example, 2:1 to 3:1, for another example, 2.0:1 to 2.5:1, and for still another example, 2.1:1 to 2.3:1.

In some embodiments, the hydrochloride solution of the compound shown in formula I is obtained by mixing a raw material comprising a solution of the compound shown in formula I and a concentrated hydrochloric acid solution; for example, the hydrochloride solution of the compound shown in formula I is a mixture of the raw material consisting of the solution of the compound shown in formula I and the concentrated hydrochloric acid solution.

For example, the solvent of the solution of the compound shown in formula I is a mixture of the organic solvent and water; for another example, the solution of the compound shown in formula I is a mixture of the compound shown in formula I, the organic solvent and water.

For example, the organic solvent and water have a volume ratio of 5-15:0.5-1.5, for another example, 10:1 to 6:1, for still another example, 10:1 to 8:1, and for yet another example, 9:1.

For example, the solution of the compound shown in formula I is obtained by mixing the compound shown in formula I and the solvent at a temperature of 30 to 70° C., and the temperature is, for example, 40 to 60° C., and for another example, 45 to 55° C.

The present disclosure also provides a preparation method for the crystal form A of the hydrochloride hydrate of the compound shown in formula I, comprising the following steps: precipitating a crystal from a hydrochloride solution of the compound shown in formula I, the crystal being crystal form A; wherein the hydrochloride solution of the compound shown in formula I contains the compound shown in formula I, an organic solvent, water and a concentrated hydrochloric acid solution, and the organic solvent is one or a mixture of two or more selected from methanol, ethanol, n-propanol, n-butanol, isopropanol, isobutanol and tert-butanol. Two or more here should be understood as including two. It should be clear to those skilled in the art that the hydrochloride solution of the compound shown in formula I does not contain other organic solvents, except for unavoidable impurities or solvent residues.

In some embodiments, the organic solvent is ethanol.

In some embodiments, the hydrochloride solution of the compound shown in formula I is a mixture of the compound shown in formula I, the organic solvent, water and the concentrated hydrochloric acid solution.

In some embodiments, the concentrated hydrochloric acid solution and the compound shown in formula I have a ratio of 0.38 mL-0.57 mL:1 g, for example, 0.4 mL-0.5 mL:1 g, for another example, 0.38 mL-0.40 mL:1 g, 0.40 mL-0.42 mL:1 g, 0.42 mL-0.44 mL:1 g, 0.44 mL-0.46 mL:1 g, 0.46 mL-0.48 mL:1 g, 0.48 mL-0.50 mL:1 g, 0.50 mL-0.52 mL:1 g, 0.52 mL-0.54 mL:1 g or 0.54 mL-0.57 mL:1 g.

In some embodiments, the organic solvent and the compound shown in formula I have a ratio of 5 mL-15 mL:1 g, for example, 8 mL-12 mL:1 g, for another example, 5 mL-6 mL:1 g, 6 mL-7 mL:1 g, 7 mL-8 mL:1 g, 8 mL-9 mL:1 g, 9 mL-10 mL:1 g, 10 mL-11 mL:1 g, 11 mL-12 mL:1 g, 12 mL-13 mL:1 g, 13 mL-14 mL:1 g, or 14 mL-15 mL:1 g.

In some embodiments, the water and the compound shown in formula I have a ratio of 0.5 mL-1.5 mL:1 g; for example, 0.8 mL-1.2 mL:1 g, and for another example, 0.5 mL-0.6 mL:1 g, 0.6 mL-0.7 mL:1 g, 0.7 mL-0.8 mL:1 g, 0.8 mL-0.9 mL:1 g, 0.9 mL-1.0 mL:1 g, 1.0 mL-1.1 mL:1 g, 1.1 mL-1.2 mL:1 g, 1.2 mL-1.3 mL:1 g, 1.3 mL-1.4 mL:1 g or 1.4 mL-1.5 mL:1 g.

In some embodiments, the organic solvent and water have a volume ratio of 5-15:0.5-1.5, preferably 10:1 to 6:1, more preferably 10:1 to 8:1, more preferably 9:1.

In some embodiments, the organic solvent, water and the compound shown in formula I have a ratio of 5 mL-15 mL:0.5 mL-1.5 mL:1 g, preferably 8 mL-12 mL:0.8 mL-1.2 mL:1 g, further preferably 9 mL:1 mL:1 g.

In some embodiments, the organic solvent, water, the concentrated hydrochloric acid solution and the compound shown in formula I have a ratio of 5 mL-15 mL:0.5 mL-1.5 mL:0.38 mL-0.57 mL:1 g, preferably 8 mL-12 mL:0.8 mL-1.2 mL:0.38 mL-0.48 mL:1 g, further preferably 9 mL:1 mL:0.41 mL:1 g.

In some embodiments, the concentrated hydrochloric acid solution has a concentration of 8 mol/L-12 mol/L, preferably 10 mol/L to 12 mol/L, more preferably 12 mol/L.

In some embodiments, in the hydrochloride solution of the compound shown in formula I, HCl and the compound shown in formula I have a molar ratio of 2:1 to 3:1, preferably 2.0:1 to 2.5:1, further preferably 2.1:1 to 2.3:1.

In some embodiments, the hydrochloride solution of the compound shown in formula I is a mixture of a solution of the compound shown in formula I and the concentrated hydrochloric acid solution.

In some embodiments, the hydrochloride solution of the compound shown in formula I is obtained by adding (for example, by dropwise addition) the concentrated hydrochloric acid solution to the solution of the compound shown in formula I.

In some embodiments, the solvent of the solution of the compound shown in formula I is a mixture of the organic solvent and water.

In some embodiments, the solution of the compound shown in formula I is obtained by mixing the compound shown in formula I and the solvent at a temperature of 30 to 70° C., and the temperature is preferably 40 to 60° C., further preferably 45 to 55° C.

In some embodiments, the solution of the compound shown in formula I is a mixture of the compound shown in formula I, the organic solvent and water.

In some embodiments, in the solvent of the solution of the compound shown in formula I, the organic solvent and water have a volume ratio of 10:1 to 6:1, preferably 10:1 to 8:1, more preferably 9:1.

In some embodiments, the preparation method further comprises: mixing the compound shown in formula I, the organic solvent and water, heating the resulting mixture to 30 to 70° C. (preferably 40 to 60° C., further preferably 45 to 55° C.), adding (for example, by dropwise addition) the concentrated hydrochloric acid solution to obtain the hydrochloride solution of the compound shown in formula I.

In some embodiments, the preparation method further comprises: stirring the hydrochloride solution of the compound shown in formula I at 30 to 70° C. The step of stirring the hydrochloride solution of the compound shown in formula I at 30 to 70° C. is performed before the step of precipitating the crystal from the hydrochloride solution of the compound shown in formula I. The stirring time is, for example, 1-5 hours, and for another example, 1 hour.

In some embodiments, the step of precipitating the crystal from the hydrochloride solution of the compound shown in formula I comprises: cooling the hydrochloride solution of the compound shown in formula I, preferably, the cooling is cooling to 20° C. to 30° C.

In some embodiments, the step of precipitating the crystal from the hydrochloride solution of the compound shown in formula I comprises: stirring the hydrochloride solution of the compound shown in formula I at 20° C. to 30° C. to precipitate the crystal. The stirring time is, for example, 48-96 hours, and for another example, 48 hours.

In some embodiments, the preparation method further comprises: after precipitating the crystal from the hydrochloride solution of the compound shown in formula I, filtering, washing and drying the resulting filter cake to obtain crystal form A.

In some embodiments, the raw materials of the preparation method only comprise the compound shown in formula I, anhydrous ethanol, water and the concentrated hydrochloric acid solution.

In some embodiments, the preparation method for the crystal form A of the hydrochloride hydrate of the compound shown in formula I further comprises: cooling the solution of the crystal form A of the hydrochloride hydrate of the compound shown in formula I for crystallization to obtain the single crystal of the crystal form A of the hydrochloride hydrate of the compound shown in formula I, wherein the solvent of the solution of the crystal form A of the hydrochloride hydrate of the compound shown in formula I is a mixture of ethanol and water.

Herein, the temperature of a mixture of ethanol and water may be 55 to 75° C., further preferably 60 to 70° C., and further preferably 64 to 66° C.

Herein, in the mixture of ethanol and water, ethanol and water may have a volume ratio of 10:1 to 6:1, preferably 10:1 to 8:1, more preferably 9:1.

Herein, the cooling may be cooling to 20° C. to 30° C.

The present disclosure also provides a hydrochloride hydrate of a compound shown in formula I. In the hydrochloride hydrate, the compound shown in formula I, HCl and water have a molar ratio of 1:x:y, x being greater than 0 but not greater than 3, and y being greater than 0 but not greater than 3.

In some embodiments, in the hydrochloride hydrate, the compound shown in formula I, HCl and water have a molar ratio of 1:2:2.

The present disclosure also provides a pharmaceutical composition comprising at least one of the hydrochloride hydrate of the compound shown in formula I described in any of the above embodiments and the crystal form A of the hydrochloride hydrate of the compound shown in formula I described in any of the above embodiments, and at least one pharmaceutically acceptable carrier.

In some embodiments, the carrier is at least one of an excipient, a diluent and a solvent.

The present disclosure also provides a use of the hydrochloride hydrate of the compound shown in formula I, the crystal form A or the pharmaceutical composition described in any of the above embodiments in manufacturing a medicament for preventing or treating a Janus kinase-mediated disorder, disease or condition.

The present disclosure also provides a method for preventing or treating a Janus kinase-mediated disorder, disease or condition in a subject in need thereof, comprising administering to the subject a prophylactically or therapeutically effective amount of the hydrochloride hydrate of the compound shown in formula I, the crystal form A or the pharmaceutical composition described in any of the above embodiments.

The present disclosure also provides the hydrochloride hydrate of the compound shown in formula I, the crystal form A or the pharmaceutical composition described in any of the above embodiments for use in preventing or treating a Janus kinase-mediated disorder, disease or condition.

In some embodiments, the Janus kinase is at least one of JAK1, JAK2, JAK3, and TyK2.

In some embodiments, the Janus kinase-mediated disease is at least one of a hyperproliferative disease, a cancer (e.g., leukemia and lymphoma), and immune and inflammatory condition (e.g., transplant rejection, asthma, chronic obstructive pulmonary disease, allergy, rheumatoid arthritis, psoriasis, atopic dermatitis, Crohn's disease, ulcerative colitis, amyotrophic lateral sclerosis, and multiple sclerosis).

In some embodiments, the Janus kinase-mediated disease is at least one of leukemia, lymphoma, transplant rejection, asthma, chronic obstructive pulmonary disease, allergy, rheumatoid arthritis, psoriasis, atopic dermatitis, Crohn's disease, ulcerative colitis, amyotrophic lateral sclerosis and multiple sclerosis.

On the basis of not violating the common sense in the art, the above-mentioned preferred conditions can be arbitrarily combined to obtain the preferred embodiments of the present disclosure.

The reagents and raw materials used in the present disclosure are commercially available.

The positive progress effect of the present disclosure lies in that the salt form and the crystal form of the present disclosure have good JAK kinase inhibitory activity, solubility, stability and bioavailability, which enhance the developability of the oral preparation of the compound shown in formula I.

Definition and Description

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable carrier" used herein refers to a pharmaceutical excipient, which refers to all substances contained in pharmaceutical preparations except for active ingredients, such as the pharmaceutical excipient specified in Part IV of the Pharmacopoeia of the People's Republic of China (2015 or 2020 edition).

The term "pharmaceutical composition" used herein refers to a composition that contains a specified active ingredient and can be prepared in the same dosage form.

The term "subject" used herein refers to any animal that will or has received administration of the compound or the composition according to the embodiment of the present disclosure, the subject is preferably mammals, more preferably humans. As used herein, the term "mammal" includes any mammal. Examples of mammals include, but are not limited to, cattle, horses, sheep, pigs, cats, dogs, mice, rats, rabbits, guinea pigs, monkeys, humans, etc., and most preferably humans.

As used herein, the term "prophylactically or therapeutically effective amount" refers to an amount of compound that, when administered to a subject, is sufficient to effectively prevent or treat the disorders, diseases or conditions described herein. The amount of a compound constituting a "prophylactically or therapeutically effective amount" varies depending on the compound, the type and severity of the disorder, disease or condition, and the age of the subject, but can be adjusted as needed by those skilled in the art.

The term "treatment" as used herein refers to a therapeutic therapy. Regarding to a specific disease or condition, the "treatment" refers to at least one of the following: (1) alleviation of one or more biological manifestations of a disorder, disease or condition, (2) interfering with one or more biological manifestations of the disorder, disease or condition, (3) improvement or elimination of one or more symptoms, effects or side effects associated with the disorder, disease or condition, or one or more symptoms, effects or side effects associated with the treatment of the disorder, disease or condition, and (4) slowdown of the progression of one or more biological manifestations of the disorder, disease or condition.

The present disclosure employs the following abbreviations:

XRPD X-ray powder diffraction
DSC Differential scanning calorimetry
TGA Thermogravimetric analysis
rpm revolution(s) per minute
ATP Adenosine triphosphate
DTT DL-dithiothreitol
SEB Supplier of Enzymatic Buffer, enzyme reaction buffer additive
AUClast Area under blood drug concentration-time curve
Cmax Peak concentration
min Minute(s)
–RH Relative humidity XRPD Characterization Method Unless otherwise specified, each XRPD data (including but not limited to XRPD patterns shown in FIGS. 1,4-5, and 8-12) described in the present disclosure were determined by the following conditions:

Sample preparation: An appropriate amount of the sample to be tested was taken and evenly distributed in a sample holder, flattened with a clean glass plate so that the surface of the sample was flush with the surface of the sample holder.

The instrument used was a Bruker D2 Phaser X-ray powder diffractometer, wherein the detector: PSD LynxEye detector Diffractometer parameter settings: goniometer diameter, 282.2 mm; divergence slit, 1.0 mm; main soller slit, 2.5 degrees; secondary soller slit, 2.5 degrees; anti-air scattering component, 1.0 mm; light tube element, copper; light tube parameters, voltage of 30 kV, current of 10 mA;

scan parameter settings: scan type, Locked coupled; scan mode, Continuous PSD fast mode; rotation speed, 20 degrees/min; scan range, 3 degrees to 40 degrees (2θ); scan step, 0.02 degrees (2θ); scan speed, 0.2 sec/step; detector opening, 4.5 degrees.

DSC Characterization Method

Unless otherwise specified, DSC data described in the present disclosure were determined by the following conditions:

Instrument: Discovery DSC250 differential scanning calorimeter, and sample tray type was pierced hole;

the heating range was 25° C. to 300° C., and the heating rate was 10° C./min;

TGA Characterization Method

Unless otherwise specified, TGA data described in the present disclosure were determined by the following conditions:

Instrument: Discovery 55 thermogravimetric analyzer sample tray type: default open aluminum tray;

heating range: 10° C. to 300° C., heating rate was 10° C./min.

BRIEF DESCRIPTION OF THE DRAWINGS

In FIGS. 1, 4-5, 8-12 and 14, the unit of ordinate intensity is counts, the unit of abscissa 2θ angle is degree (°), and the unit of abscissa 2θ angle in FIGS. 6-7 is degree (°).

DETAILED DESCRIPTION OF THE PREFERRED EMBODIMENT

Figure 1:
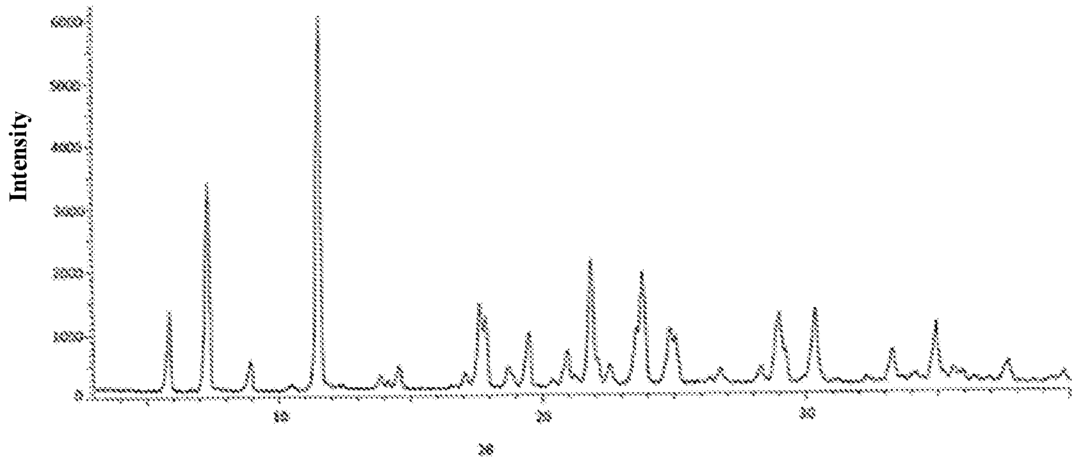
FIG. 1 is an XRPD pattern of a crystal form A.

The present disclosure will be further described below with reference to embodiments, but the present disclosure is not therefore limited to the scope of the embodiment. Experimental methods without specific conditions in the following embodiments are selected according to conventional methods and conditions, or according to the commercial specification.

In the following embodiments, unless otherwise specified, the mass spectrum was detected by Waters Acquity Xevo G2-XS QT of UPLC/MS ultra-high performance liquid chromatography high-resolution mass spectrometry system, and $^{1}$H-NMR was detected by Bruker AVANCE III 400 MHz nuclear magnetic resonance instrument or Bruker AVANCE III HD 300 MHz nuclear magnetic resonance instrument, and HPLC was detected by Agilent 1260 high performance liquid chromatography.

Unless otherwise specified, the concentrated hydrochloric acid solution mentioned in the present disclosure refers to an aqueous solution of hydrogen chloride (HCl), with a concentration of not less than 8 mol/L.

Unless otherwise specified, room temperature in the present disclosure refers to 20 to 30° C.

Embodiment 1. Synthesis of Compound Shown in Formula I

Synthesis of Compound 4

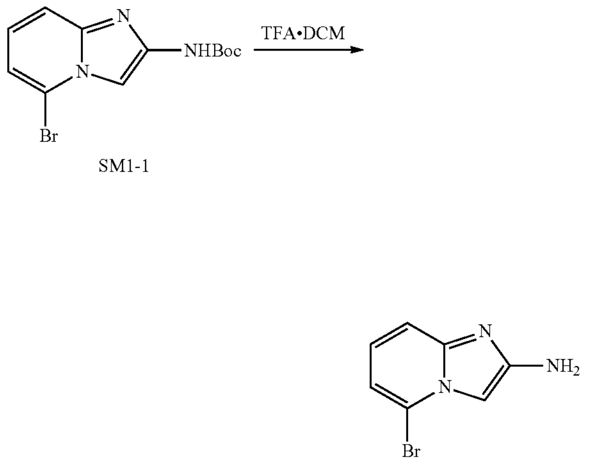

SM1-1

4

SM1-1 (54.60 g, 175.0 mmol) and dichloromethane (1 L) were added to a 3 L round bottom flask, cooled to 0° C., and then trifluoroacetic acid (200 mL) was slowly added dropwise thereto. After the dropwise addition, the mixture was stirred at room temperature for 10 hours. HPLC showed that the reaction was complete, and the trifluoroacetic acid was removed under vacuum, then diluted with dichloromethane (500 mL). The resulting solution was washed with $NaHCO_3$ aqueous solution, then dried and concentrated, and purified by silica gel column chromatography to obtain compound 4 as a white solid (23.00 g, yield of 62.0%).

NMR data of compound 4: $^{1}$H NMR (400 MHz, DMSO-$d_6$) δ ppm: 7.24 (d, J=8.4 Hz, 1H), 7.05 (dd, J=1.1 Hz, 6.8 Hz, 1H), 6.97-7.01 (m, 2H), 5.31 (br, 2H).

Synthesis of Compound 5

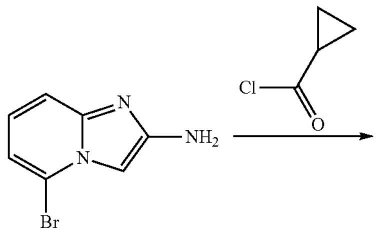

4

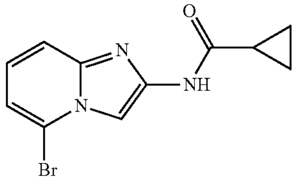

5

Compound 4 (23.00 g, 108.5 mmol), triethylamine (39.46 g, 390.0 mmol) and acetonitrile (400 mL) were added to a 2 L round bottom flask. After cooling to 0° C., cyclopropanecarbonyl chloride (40.23 g, 384.9 mmol) was slowly added dropwise thereto. After the dropwise addition, the mixture was stirred at room temperature for 8 hours, and HPLC showed that the reaction was complete. The resulting reaction solution was concentrated to dryness, then washed with water, and filtered to obtain a solid. The resulting solid was subjected to column chromatography to obtain compound 5 as a white solid (29.46 g, yield of 97.0%).

NMR data of compound 5: $^1H$ NMR (400 MHz, DMSO-$d_6$) δ ppm: 11.14 (br, 1H), 8.05 (s, 1H), 7.50-7.52 (m, 1H), 7.19-7.28 (m, 2H), 1.92-1.99 (m, 1H), 0.82-0.84 (m, 4H).

Synthesis of Compound Shown in Formula I

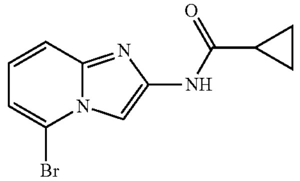

+

5

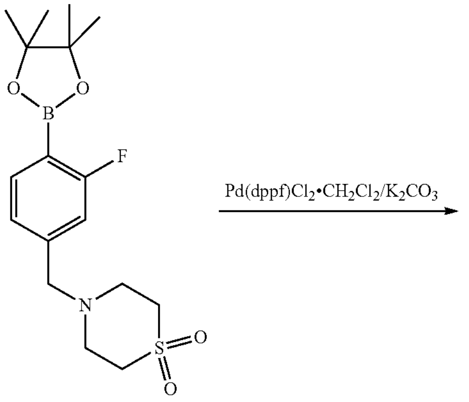

SM2-1

-continued

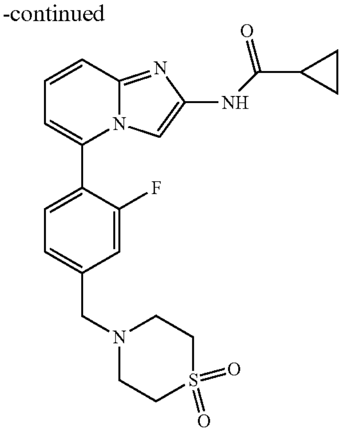

I

Compound 5 (29.46 g, 105.2 mmol), SM2-1 (41.88 g, 113.4 mmol), $K_2CO_3$ (26.12 g, 189.0 mmol), Pd(dppf)$Cl_2$·$CH_2Cl_2$ (6.91 g, 8.5 mmol), $H_2O$ (120 mL) and 1,4-dioxane (600 mL) were added to a 2 L round bottom flask. The mixture was heated to reflux under $N_2$ protection for 10 hours. HPLC showed that the reaction was complete, and the reaction was quenched by adding ice water and filtered to obtain a solid. The resulting solid was subjected to column chromatography to obtain the compound shown in formula I (27.42 g, yield of 58.9%), which was a white solid.

Characterization data of the compound shown in formula I: $^1H$ (400 Hz, DMSO-$d_6$) δ ppm: 8.08 (1H, dd, J=9.2, 7.3 Hz), 8.03 (1H, dd, J=9.3, 1.6 Hz), 7.84-7.78 (3H, m), 7.60 (1H, dd, J=7.1, 1.6 Hz), 4.66 (2H, s), 3.90-3.89 (4H, m), 3.70-3.68 (4H, m), 1.97-1.94 (1H, m), 1.08-1.04 (4H, m). LC/MS m/z: 443.2 (M+H).

Embodiment 2. Preparation of Crystal Form A of Hydrochloride Hydrate of the Compound Shown in Formula I The compound shown in formula I (1.5 g, 3.4 mmol) was added to a round bottom flask, then 13.5 mL of anhydrous ethanol and 1.5 mL of pure water were added thereto, and the resulting mixture was stirred and heated to 50° C. Then 0.62 mL of concentrated hydrochloric acid solution (12 mol/L, 7.4 mmol) was added dropwise thereto. After the dropwise addition, the resulting hydrochloride solution of the compound shown in formula I was kept at 50° C. and stirred for 1 hour, and then cooled naturally to 25° C. at room temperature, then kept at 25° C. and stirred for 48 hours to precipitate a crystal, and the stirring was stopped. The mixture was filtered, and the resulting filter cake was washed with a small amount of ethanol, collected, and dried under vacuum at 40° C. for 6 hours, and the resulting crystal was crystal form A.

The XRPD pattern of crystal form A is shown in FIG. 1, wherein the X-ray powder diffraction peaks expressed in 2θ angles are shown in Table 1.

Figure 2:
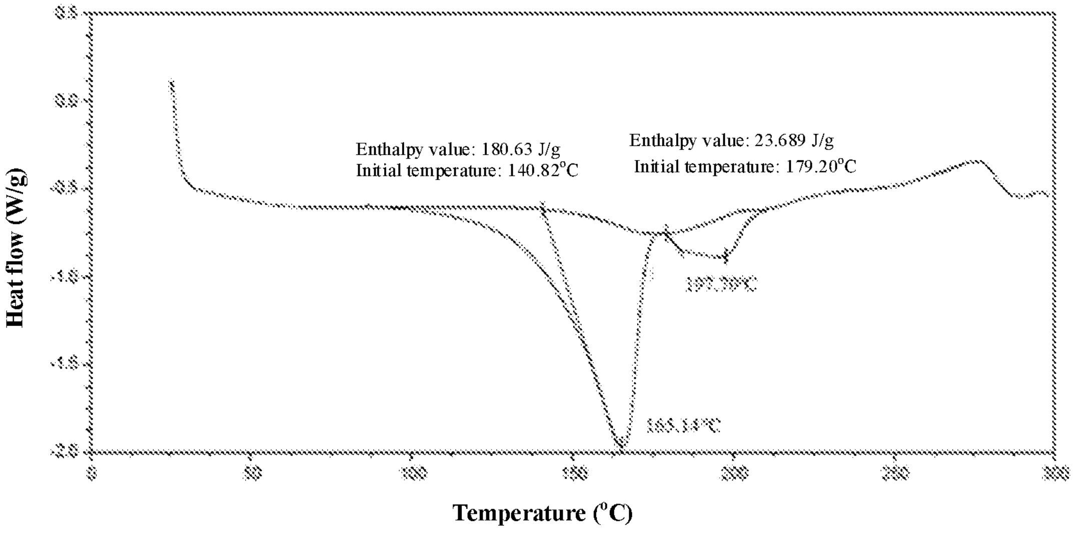
FIG. 2 is a DSC pattern of the crystal form A.

DSC results of the crystal form A are shown in FIG. 2. DSC shows a first endothermic peak at 165.14° C. with an enthalpy value of 180.63 J/g and an initial temperature of 140.82° C.; the other endothermic peak is at 197.70° C. with an enthalpy value of 23.689 J/g and an initial temperature of 179.20° C.

Figure 3:
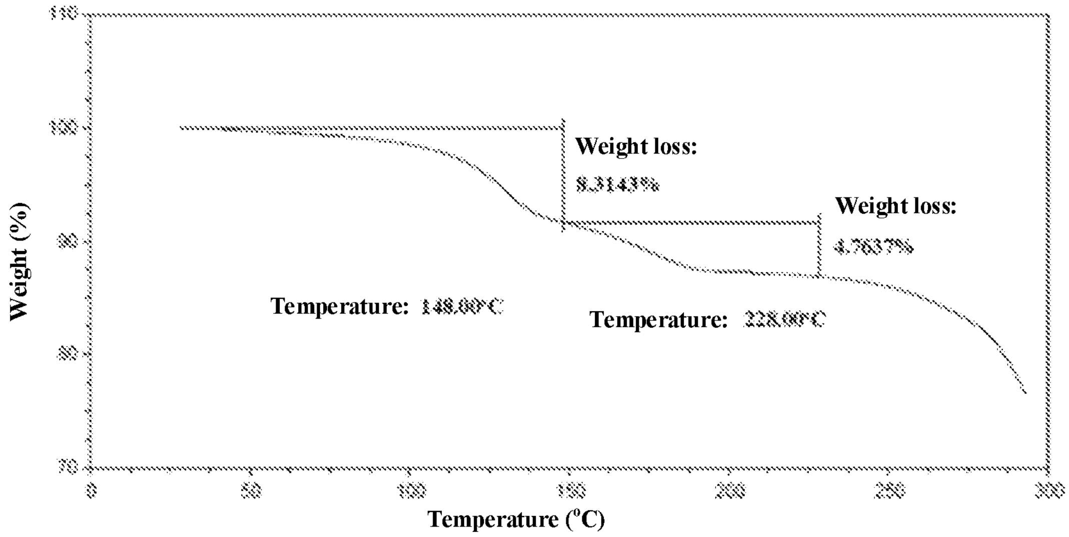
FIG. 3 is a TGA pattern of the crystal form A.

TGA results of the crystal form A are shown in FIG. 3, which shows that the sample has a weight loss of 8.3143% before 148.00° C.; and a weight loss of 4.7637% at 148 to 228° C.

The content of chloride ion was determined by Mettler-Toledo T5 potentiometric titrator, and the results showed that the content of chloride ion in the sample was 12.3%, which was basically consistent with the sample containing two chloride ions (the theoretical value of chloride ion in the sample containing two hydrochloride was 12.9%). Water content was determined by Mettler-Toledo KF Titrator V30S, and the results showed that the water content in the sample was 8.0%, which was basically consistent with the sample containing two crystal waters (the theoretical value of water content in the sample containing two crystal waters was 6.5%). It can thus be confirmed that the crystal form A is the hydrochloride hydrate of the compound shown in formula I, and in the hydrochloride hydrate, the compound shown in formula I, HCl and water have a molar ratio of 1:2:2.

Figure 4:
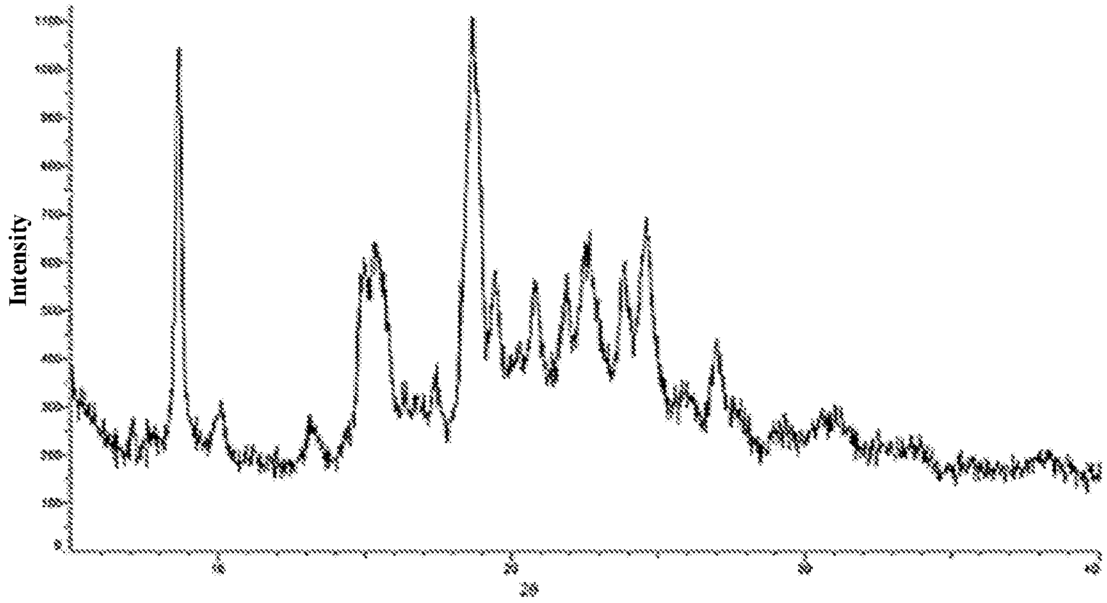
FIG. 4 is an XRPD pattern of a crystal form C.

Comparative Embodiment 1. Attempts to Prepare Crystal Form a with Other Solvent Systems (1) Crystallization in THF/Water System The compound shown in formula I (1.0 g, 2.3 mmol) was added to a round bottom flask, then 9 mL of THF and 1 mL of pure water were added thereto, and the resulting mixture was stirred and heated to 60° C. Then 0.41 mL of concentrated hydrochloric acid solution (12 mol/L, 4.9 mmol) was added dropwise thereto. After the dropwise addition, the resulting hydrochloride solution of the compound shown in formula I was kept at 60° C. and stirred for 1 hour, and then cooled naturally to 25° C. at room temperature, then kept at 25° C. and stirred for 48 hours to precipitate a crystal, and the stirring was stopped. The mixture was filtered, and the resulting filter cake was washed with a small amount of THF and then dried. The resulting solid was crystal form C, and an XRPD pattern of crystal form C is shown in FIG. 4. It can be seen that the resulting crystal form C is different from crystal form A.

(2) Crystallization in DCM/MeOH System

Figure 5:
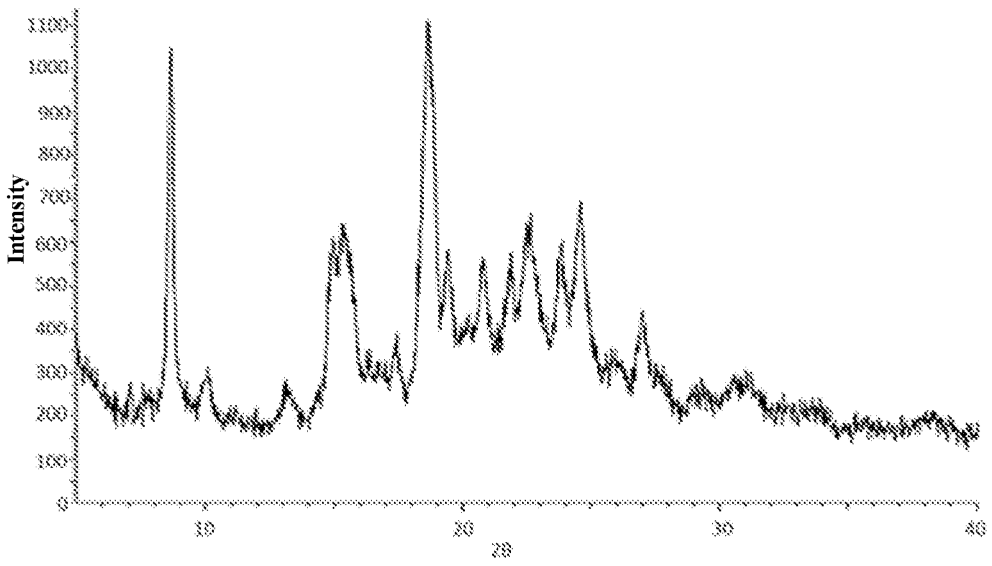
FIG. 5 is an XRPD pattern of a crystal form D.

The compound shown in formula I (0.5 g, 1.1 mmol) was added to a round bottom flask, then 10 mL of DCM and 10 mL of MeOH were added thereto, and the resulting mixture was stirred and heated to 40° C. Then 4M hydrochloric acid solution (0.6 mL, 2.4 mmol) was added dropwise thereto. After the dropwise addition, the resulting hydrochloride solution of the compound shown in formula I was kept at 40° C. and stirred for 1 hour, and then cooled naturally to 25° C. at room temperature, then kept at 25° C. and stirred for 48 hours to precipitate a crystal, and the stirring was stopped. The mixture was filtered, and the resulting filter cake was washed with a small amount of DCM and then dried. The resulting solid was crystal form D, and an XRPD pattern of crystal form D is shown in FIG. 5. It can be seen that the resulting crystal form D is different from crystal form A.

Figure 6:
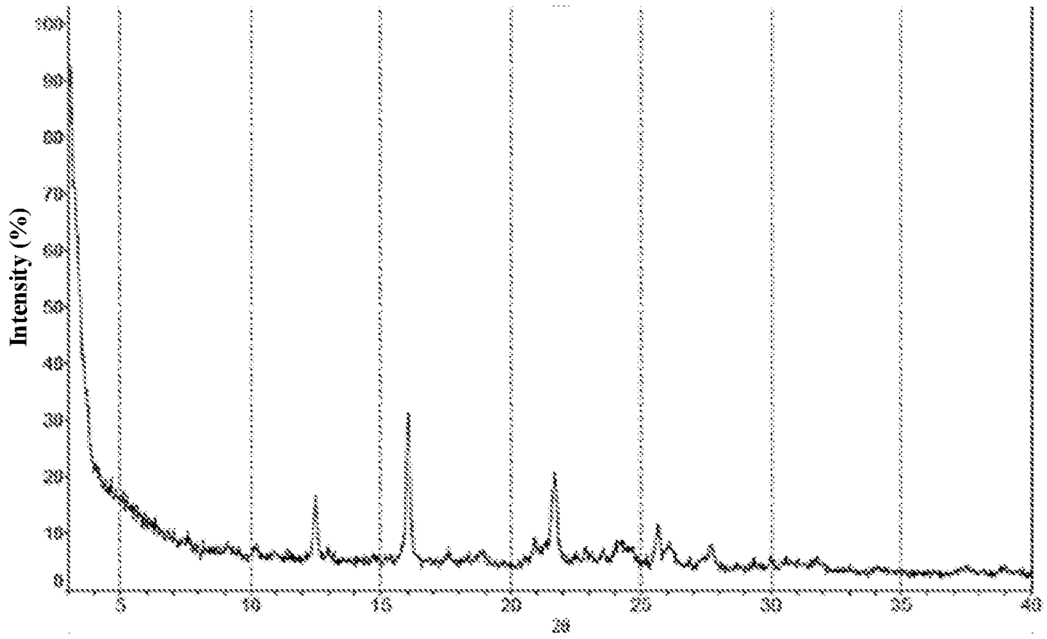
FIG. 6 is an XRPD pattern of a crystal form E.

Comparative Embodiment 2. Preparation of Hydrochloride Crystal Form E of the Compound Shown in Formula I 10 mg of crystal form A of hydrochloride hydrate of the compound shown in formula I was added to 0.3 mL of acetonitrile, stirred at room temperature for 3 days, and filtered to obtain crystal form E. The XRPD pattern of crystal form E is shown in FIG. 6.

The detection instrument used in the XRPD pattern shown in FIG. 6 of the present disclosure was Bruker D8 Advance X-ray diffractometer, wherein, X-ray tube parameters were set as follows: X-ray wavelength, Cu: K-Alpha ($\lambda$=1.54179 Å); voltage, 40 kV; current, 40 mA; sample rotation speed: 15 rpm; scanning range: 3 to 40 degrees (2θ); scanning speed: 10 degrees/min.

Figure 7:
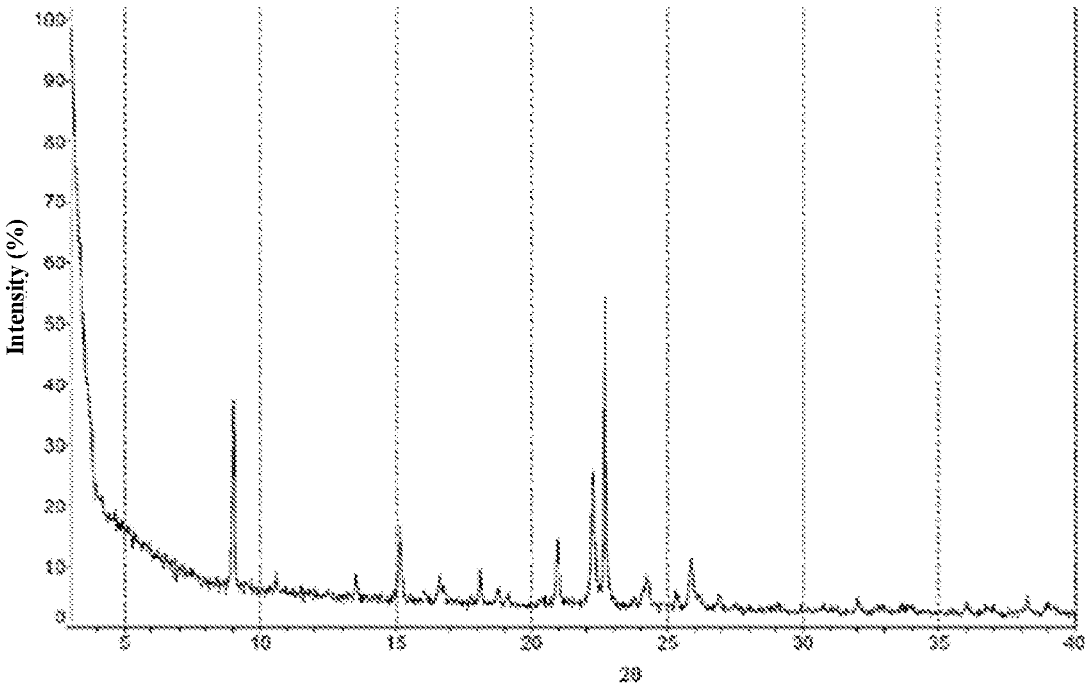
FIG. 7 is an XRPD pattern of a crystal form F.

Comparative Embodiment 3. Preparation of Hydrochloride Crystal Form F of the Compound Shown in Formula I 10 mg of crystal form A of hydrochloride hydrate of the compound shown in formula I was added to a 4 mL vial, added to 0.5 mL of DMSO, and stirred to dissolve. Another 40 mL round bottom flask was taken and added with 4 mL of acetonitrile. The vial was placed in a round bottom flask, which was capped and left to crystallize slowly at room temperature. After 3 days, the crystal form F was obtained by filtration, and the XRPD pattern of the crystal form F is shown in FIG. 7.

The detection instrument used in the XRPD pattern shown in FIG. 7 of the present disclosure was Bruker D8 Advance X-ray diffractometer, wherein, X-ray tube parameters were set as follows: X-ray wavelength, Cu: K-Alpha ($\lambda$=1.54179 Å); voltage, 40 kV; current, 40 mA; sample rotation speed: 15 rpm; scanning range: 3 to 40 degrees (20); scanning speed: 10 degrees/min.

Embodiment 3. JAK Kinase Inhibitory Activity Test of Crystal Form A of Hydrochloride Hydrate of Compound Shown in Formula I Cisbio's HTRF® (Homogeneous Time-Resolved Fluorescence) kit (HTRF kinEASE-TK kit, catalog number: 62TKOPEC) was used for in vitro enzyme activity biochemical assay of the compound, and the substrate, kinase reaction buffer, detection buffer, allophycocyanin modifier (XL-665)-labeled streptavidin, europium (EU)-labeled specific phosphorylated antibody and SEB were all included in the kit. JAK1 used in the assay was purchased from Invitrogen (catalog number: PV4774), JAK2, JAK3 and TYK2 were purchased from Carna Biosciences, Inc. (catalog numbers: 08-045, 08-046, 08-147, respectively), and DTT was purchased from Sigma (catalog number: 43816).

The compound (the crystal form A of the hydrochloride hydrate of the compound shown in formula I prepared according to the method in embodiment 2 or Tofacitinib citrate (Shanghai Haoyuan Chemexpress Co., Ltd., HY-40354A)) was 3-fold serially diluted 10 times in DMSO, and the concentration of the resulting compound diluent was 100-fold of the final test concentration. Then, the concentration of the compound diluent was further diluted to 2.5-fold of the final test concentration with the kinase reaction buffer to obtain a compound solution to be tested.

An enzymatic reaction was carried out in a white 384-well polypropylene plate (Greniner, catalog number: 784075) in a total reaction volume of 10 μL containing 500 ng/mL JAK1, 6 ng/mL JAK2, 37 ng/mL JAK3, 100 ng/mL TYK2, 1 μM substrate and 1 mM ATP (Sigma-Aldrich, catalog number: A7699).

4 μL of the compound solution to be tested was added to the wells of the 384-well polypropylene plate, then 2 μL of JAK1 (with additional addition of buffer additives $MgCl_2$, $MnCl_2$ and DTT, each at a final concentration of 5 mM, 1 mM and 1 mM, respectively), JAK2 (with additional addition of buffer additives $MgCl_2$ and DTT, each at a final concentration of 5 mM and 1 mM, respectively), JAK3 (with additional addition of buffer additives $MgCl_2$ and DTT, each at a final concentration of 5 mM and 1 mM, respectively), JAK3 (with additional addition of buffer additives $MgCl_2$ and DTT, each at a final concentration of 5 mM and 1 mM, respectively), TYK2 (with additional addition of buffer additives $MgCl_2$, $MnCl_2$, DTT and SEB, each at a final concentration of 5 mM, 1 mM, 1 mM and 12.5 nM, respectively) diluted in kinase reaction buffer were added thereto, and incubated at room temperature for 15 minutes for pretreatment. The enzymatic reaction was initiated by adding a mixture of 2 μL of substrate and 2 μL of ATP prepared in kinase reaction buffer. After 30 minutes of reaction at room temperature, 5 μL of allophycocyanin modifier (XL-665)-labeled streptavidin prepared in detection buffer and 5 μL of europium-labeled specific phosphorylated antibody prepared in detection buffer were added thereto to stop the enzymatic reaction and generate a signal. After incubation for 1 hour at room temperature, the plate was read in a Molecular Devices SpectraMAX Paradigm multiplate reader with the following settings: excitation at 340 nm/emission 1 at 616 nm/emission 2 at 665 nm. The ratio of the emitted optical signals of the acceptor and donor for each well was calculated according to the following formula: Ratio=signal 665 nm/signal 616 nm*10000, wherein signal 665 nm is the signal at 665 nm, and signal 616 nm is the signal at 616 nm. The percentage of inhibition was calculated according to the formula: percentage of inhibition=100%−ratio value of a treated compound/ratio value of a treated DMSO carrier (DMSO carrier was a blank control group without drugs).

A dose-response curve was generated, and $IC_{50}$ was calculated by non-linear S-shaped curve fitting using GraphPad Prism software. The resulting results are as follows:

TABLE 2

$IC_{50}$ data of crystal form A of hydrochloride hydrate of the compound shown in formula I

| | $IC_{50}$ (nM) | | | |
|---|---|---|---|---|
| Compound | JAK1 | JAK2 | JAK3 | TYK2 |
| Tofacitinib citrate | 33.13 | 103.9 | 87.24 | 1294 |
| Crystal form A | 144.9 | 461.7 | 5522 | 652.9 |

Embodiment 4. Solubility Test of Compound Shown in Formula I and Crystal Form A The sample that has been ground into fine powder was weighed and added to a certain volume of solvent (ambient temperature: 25° C.±5° C.), shaken strongly for 30 seconds every 5 minutes, and the dissolution was observed within 30 minutes. If there were no visually visible solute particles or droplets, the sample was regarded as completely dissolved. According to this method, the dissolution of crystal form A of the hydrochloride hydrate of the compound shown in formula I and the free base form of the compound shown in formula I in common solvents was observed, and the results are shown in Table 3. Herein, "easily soluble" means that 1 g (mL) solute can be dissolved in a solvent with a volume of 1 mL≤V<10 mL; "soluble" means that 1 g (mL) solute can be dissolved in a solvent with a volume of 10 mL≤V<30 mL; "sparingly soluble" means that 1 g (mL) solute can be dissolved in a solvent with a volume of 30 mL≤V<100 mL; "slightly soluble" means that 1 g (mL) solute can be dissolved in a solvent with a volume of 100 mL≤V<1000 mL; "very slightly soluble" means that 1 g (mL) solute can be dissolved in a solvent with a volume of 1000 mL≤V<10000 mL; "almost insoluble" or "insoluble" means that 1 g (mL) solute cannot be completely dissolved in a solvent with a volume of 10000 mL.

TABLE 3

Solubility of the free base of the compound shown in formula I and crystal form A of the hydrochloride hydrate of the compound shown in formula I

| Solvent | Free base of compound shown in formula I | Crystal form A |
|---|---|---|
| Methanol | Slightly soluble | Very soluble |
| Ethanol | Slightly soluble | Soluble |
| Water | Very slightly soluble | Soluble |
| Simulated gastric juice | Insoluble | Sparingly soluble |

Embodiment 5. Stability Test of Different Crystal Forms

Figure 8:
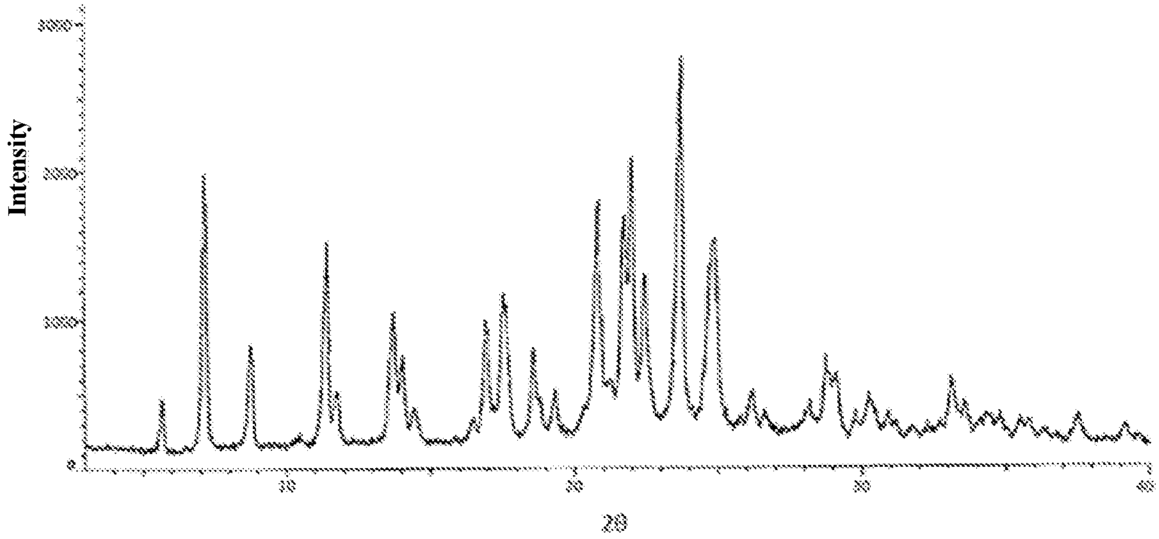
FIG. 8 is an XRPD pattern of the crystal form A placed in a stable chamber at 40° C./60%-RH for 30 days.
Figure 9:
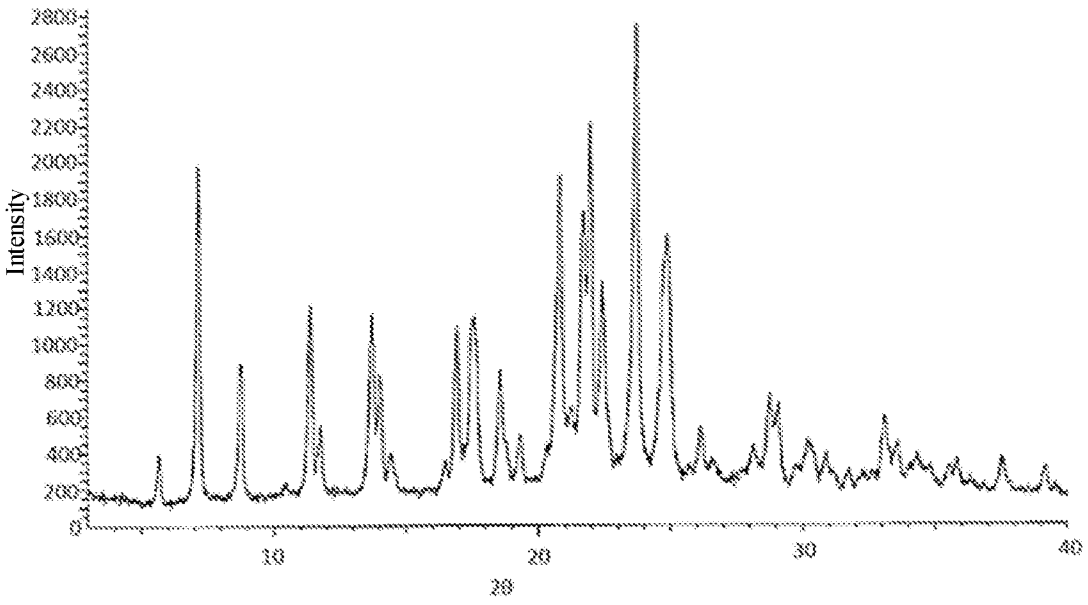
FIG. 9 is an XRPD pattern of the crystal form A placed in a stable chamber at 25° C./75%-RH for 30 days.

Whether the temperature and humidity have an impact on the stability of the crystal form A of the hydrochloride hydrate of the compound shown in formula I was tested:

The crystal form A was placed in a stable chamber, and the temperature and humidity were controlled at 40° C./60%-RH and 25° C./75%-RH, respectively. After 30 days, the resulting solid was compared with the initial crystal form A: there was no significant change in its appearance, and the content of the compound shown in formula I (as shown in Table 4) measured by HPLC had no significant change, and XRPD (see FIG. 8 and FIG. 9 for XRPD patterns obtained after treatment with 40° C./60%-RH and 25° C./75%-RH, respectively) had no significant change, showing that the crystal form A has good stability.

TABLE 4

Content of compound shown in formula I before and after placing crystal form A

| Sample | Content of compound shown in formula I |
|---|---|
| Initial crystal form A | 99.901% |
| Crystal form A placed at 40° C./75%-RH for 30 days | 99.905% |
| Crystal form A placed at 25° C./75%-RH for 30 days | 99.899% |

Figure 10:
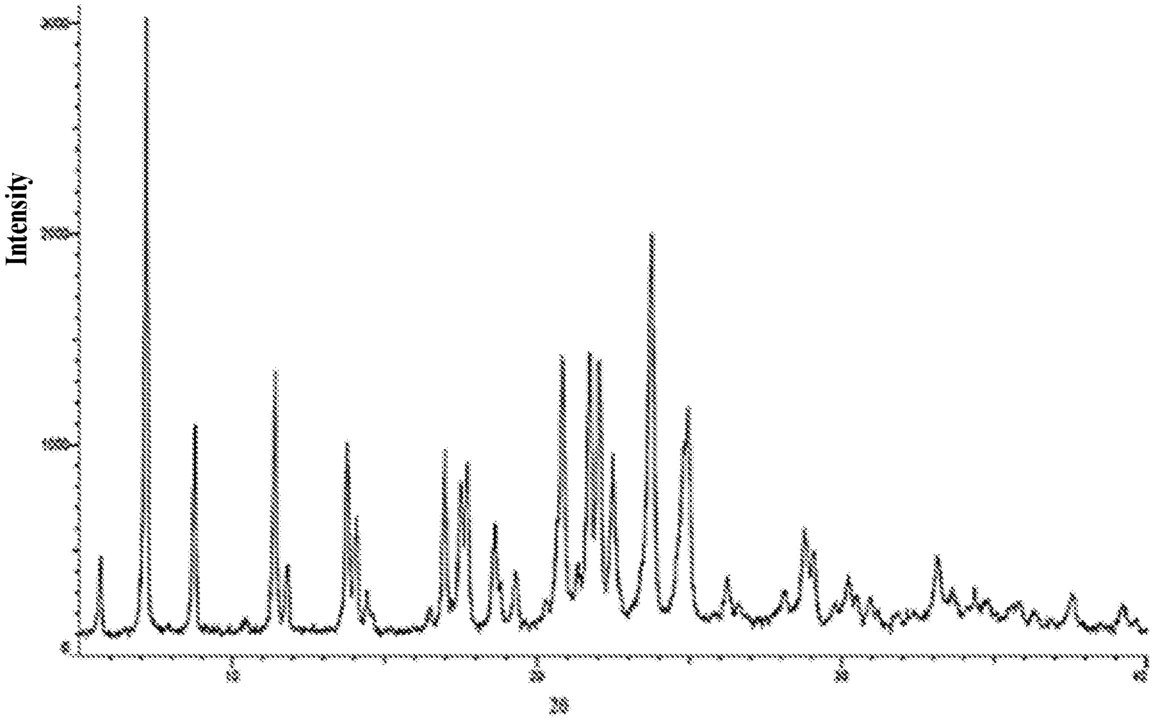
FIG. 10 is an XRPD pattern of a solid precipitated after adding the crystal form A to a saturated solution system in embodiment 5.
Figure 11:
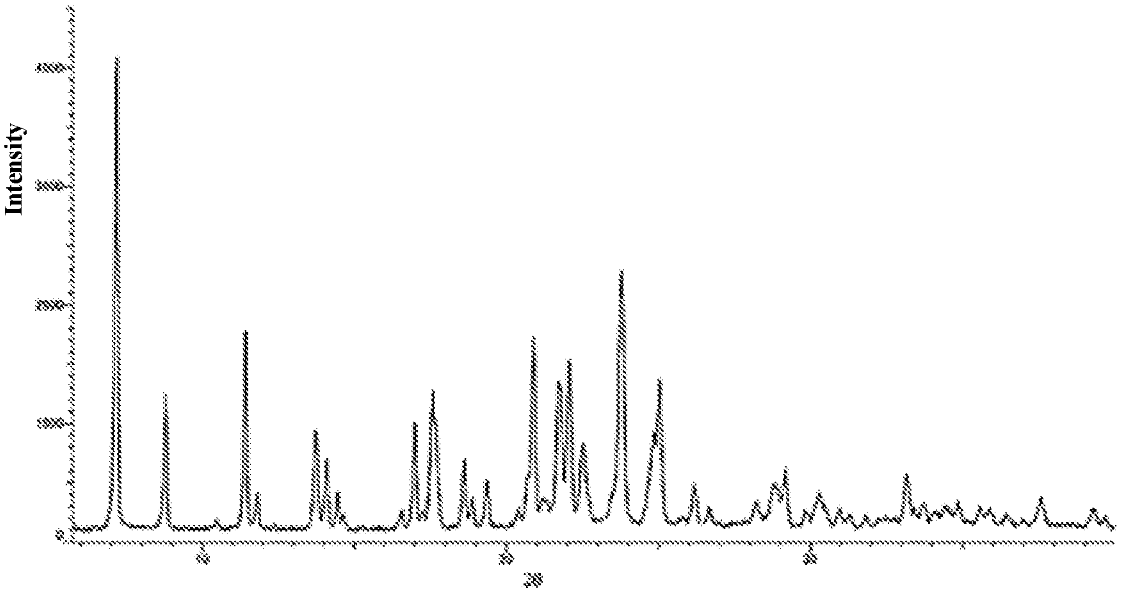
FIG. 11 is an XRPD pattern of a solid precipitated after adding the crystal form E to a saturated solution system in embodiment 5.
Figure 12:
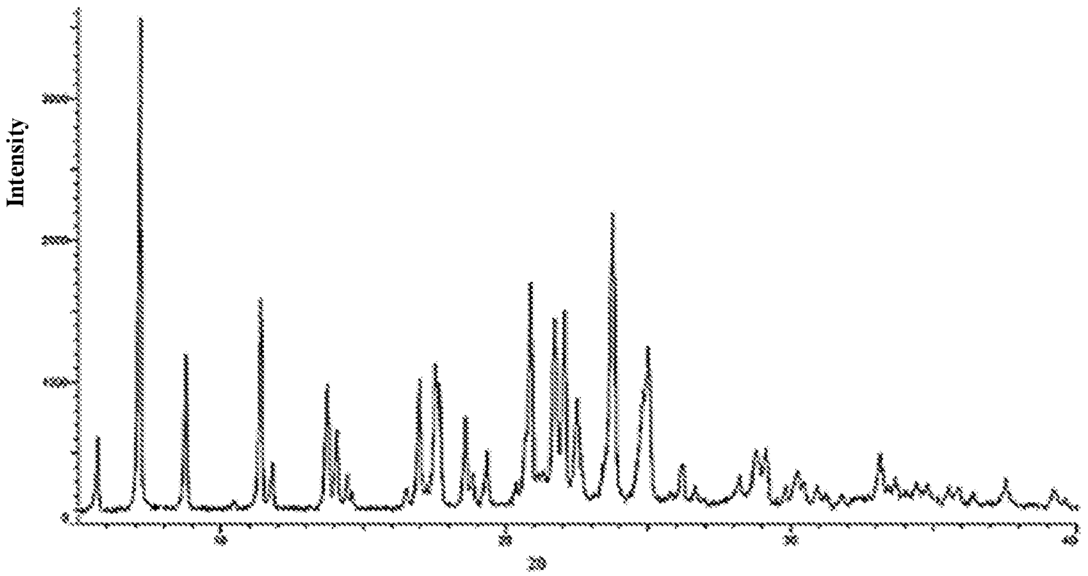
FIG. 12 is an XRPD pattern of a solid precipitated after adding the crystal form F to a saturated solution system in embodiment 5.

Comparison of thermodynamic stability of crystal form A, crystal form E and crystal form F:

Crystal form A, crystal form E and crystal form F were respectively dissolved in a mixed solvent of ethanol/water (volume ratio=9:1) to prepare a saturated solution. The saturated solution was heated to 50° C., and 10 mg of crystal form A, crystal form E and crystal form F were respectively added with stirring. The mixture was kept at 50° C., stirred for 24 hours, then filtered, and the XRPD of the resulting crystals was respectively determined (XRPD patterns of crystals precipitated by adding crystal forms A, E and F are shown in FIGS. 10, 11 and 12, respectively). The resulting XRPD pattern was compared and analyzed with the XRPD pattern of crystal form A as shown in FIG. 1, and it was found that the crystal precipitated from the system with the addition of crystal form A was still crystal form A, while both crystal form E and crystal form F were transformed into crystal form A, indicating that crystal form A has better thermodynamic stability than crystal form E and crystal form F.

Embodiment 6. Single Dose PK Study

Two groups of SD rats (3 females in each group) were given a single oral dose of 3 mg/kg free base of the compound shown in formula I and a single oral dose of 3 mg/kg crystal form A of hydrochloride hydrate of the compound shown in formula I, respectively. The drug was administered as a 0.5% CMC-Na suspension. Samples were taken at different times until 24 hours, and the drug concentration of the compound shown in formula I in plasma was analyzed by LC-MS/MS method, and the final calculation results are shown in Table 8.

Chromatographic Conditions of LC-MS/MS Method for Compound Shown in Formula I:

instrument model, SHIMADZU LC-30AD liquid phase system; chromatographic column, ACQUITY UPLC® BEH C18 (2.1×50 mm, 1.7 μm); column temperature, 40° C.; injection volume, 1 μL; flow rate of 0.6 mL/min; run time of 6 min;

the mobile phase gradient settings are shown in Table 5.

TABLE 5

| Time (min) | Mobile phase A, a solution of 0.1% formic acid in water (%) | Mobile phase B, a solution of 0.1% formic acid in acetonitrile (%) |
|---|---|---|
| 0.01 | 75 | 15 |
| 0.8 | 75 | 15 |
| 2.0 | 5 | 95 |
| 2.5 | 5 | 95 |
| 2.8 | 75 | 15 |
| 3.0 | 75 | 15 |
| 4.0 | 5 | 95 |
| 5.0 | 5 | 95 |
| 5.3 | 75 | 15 |
| 6.0 | 75 | 15 |

Mass Spectrometry Conditions

Instrument model, AB SCIEX TRIPLE QUAD 6500 mass spectrometer; ion source, electrospray (ESI); ionization mode, positive ion scanning; multi-ion (MRM) ion pairs are shown in Table 6; instrument parameters are shown in Table 7.

TABLE 6

| Analyte | Q1 mass-to-charge ratio (m/Z) | Q3 mass-to-charge ratio (m/Z) | Scan interval (ms) |
|---|---|---|---|
| Compound shown in formula I | 443.2 | 375.3 | 100 |
| GLPG0634* | 426.1 | 291.2 | 100 |

*an internal standard compound, purchased from MedChemExpress Company (catalog number: HY-18300), the same as in Table 7.

TABLE 7

| Parameter | Compound shown in formula I | GLPG0634 |
|---|---|---|
| Spray voltage (v) | 5000 | 5000 |
| Ion source temperature (° C.) | 550 | 550 |
| Collision gas (psi) | 10 | 10 |

TABLE 7-continued

| Parameter | Compound shown in formula I | GLPG0634 |
|---|---|---|
| Air curtain gas (psi) | 40 | 40 |
| Atomizing gas (psi) | 50 | 50 |
| Auxiliary gas (psi) | 40 | 40 |
| Declustering voltage (v) | 110 | 110 |
| Inlet voltage (v) | 12 | 12 |
| Collision voltage (v) | 47 | 39 |
| Outlet voltage of collision chamber (v) | 10 | 10 |

TABLE 8

PK data of crystal form A of hydrochloride hydrate of compound shown in formula I and free base of compound shown in formula I

| Solid form | AUClast | Cmax |
|---|---|---|
| Free base | 987 h*ng/mL | 352 ng/mL |
| Crystal form A | 1390 h*ng/mL | 456 ng/mL |

Embodiment 7. Study on Hygroscopicity of Crystal Form A, Crystal Form C, Crystal Form D, Crystal Form E and Crystal Form F 500 mg of each of crystal form A, crystal form C, crystal form D, crystal form E and crystal form F were taken, weighed accurately, then put in a closed container with constant humidity, placed at 25° C./75%-RH for 5 days, and then taken out to determine their hygroscopic weight gain. The results are shown in Table 9, which indicates that crystal form A has the lowest hygroscopicity.

TABLE 9

Hygroscopicity data of each crystal form

| Crystal form | Crystal form A | Crystal form C | Crystal form D | Crystal form E | Crystal form F |
|---|---|---|---|---|---|
| Hygroscopic weight gain | 2.4% | 6.1% | 8.1% | 5.3% | 4.9% |

Figure 13:
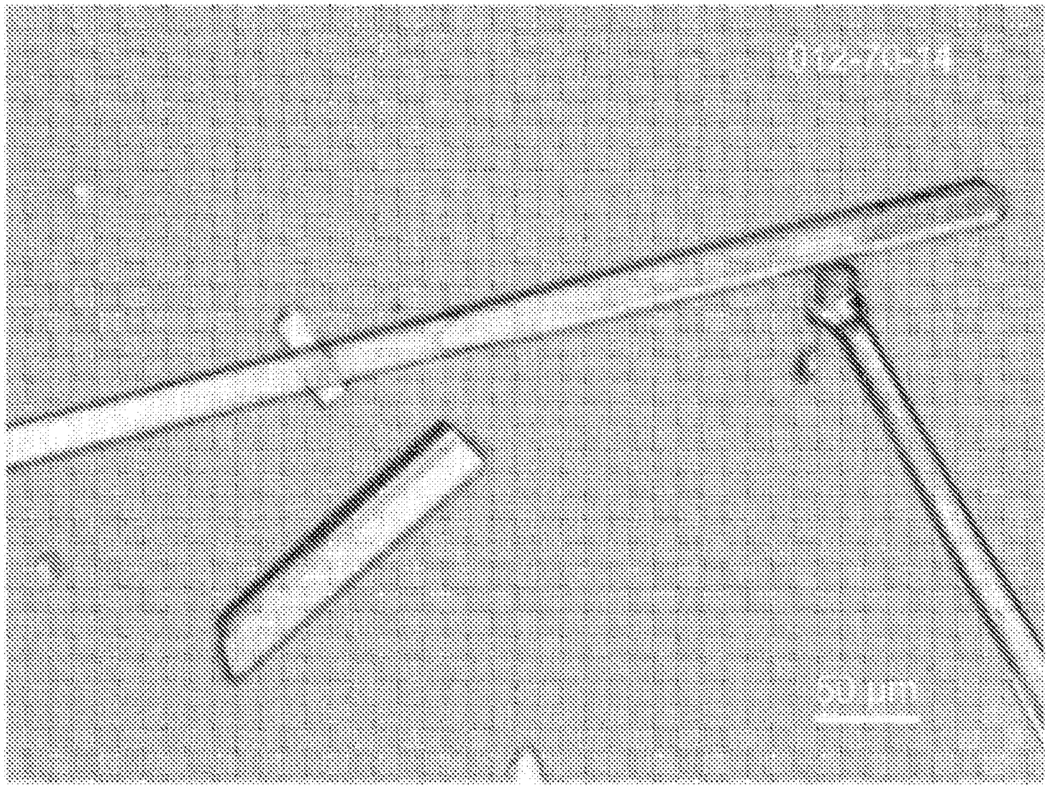
FIG. 13 shows the single crystal shape of the crystal form A obtained in embodiment 8.
Figure 14:
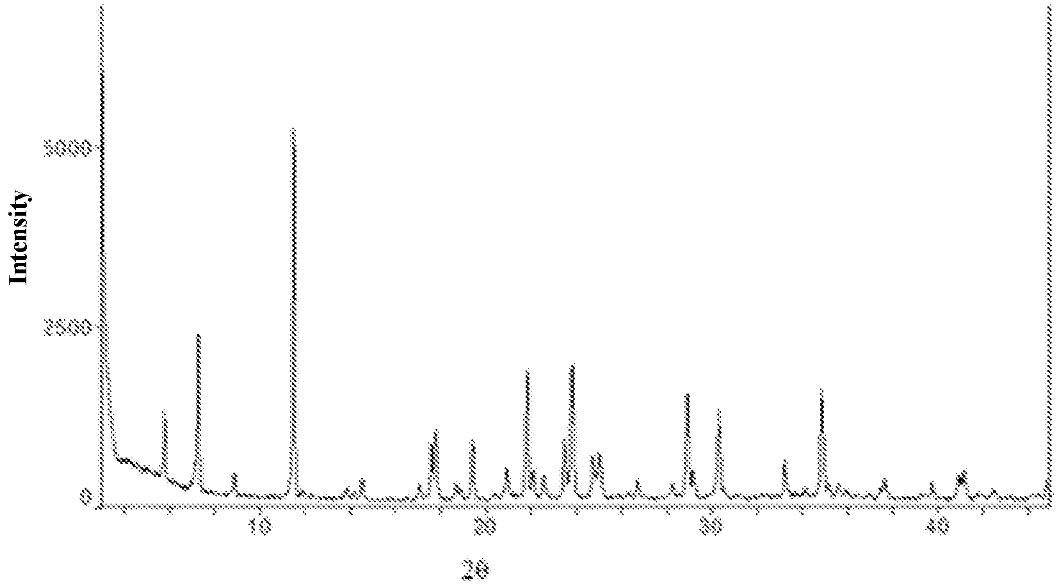
FIG. 14 is an XRPD pattern of the single crystal of the crystal form A obtained in embodiment 8.
Figure 15:
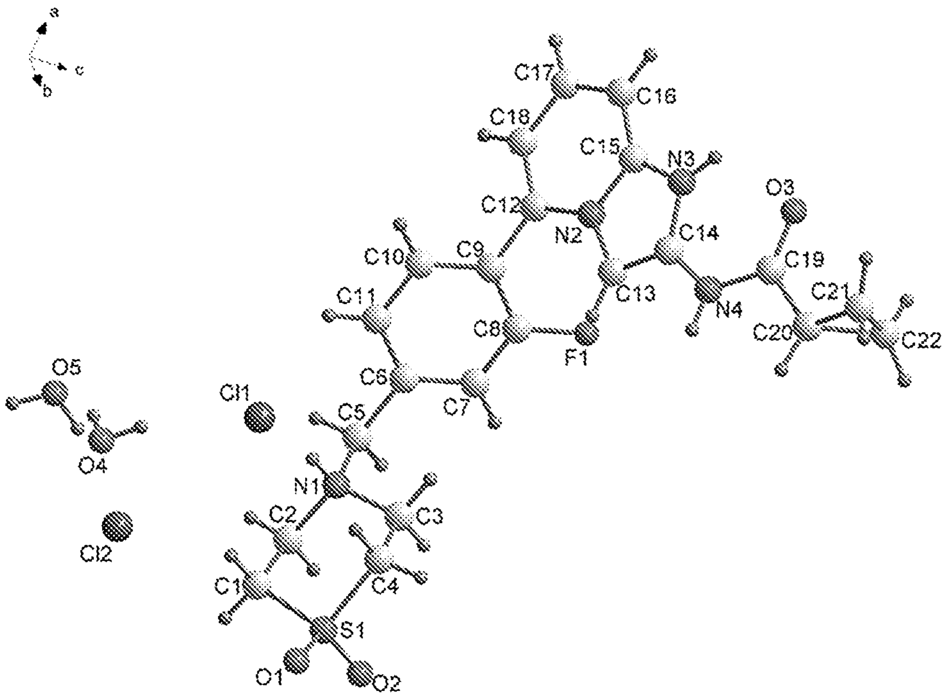
FIG. 15 is a schematic diagram of an asymmetric structural unit of the single crystal of the crystal form A obtained in embodiment 8.

Embodiment 8. Single Crystal Test and Structural Analysis of Crystal Form A 35 mg of the crystal form A sample of the hydrochloride hydrate of the compound shown in formula I prepared in embodiment 2 was weighed and dissolved in 1 mL of ethanol/water (9:1, v/v) at 65° C., and cooled to room temperature for cooling crystallization to obtain long rod-shaped crystals (FIG. 13). Then, some crystals were selected for XRPD diffraction study (FIG. 14). In FIG. 14, there are characteristic diffraction peaks at the following 2θ angles: 5.9°±0.2°, 7.4°±0.2°, 11.6°±0.2°, 21.7°±0.2° and 23.8°±0.2°, which are consistent with FIG. 1, proving that the crystal is crystal form A. The crystal was selected for single crystal test and structural analysis. The single crystal structural analysis results show that the crystal form A belongs to a monoclinic crystal system, P21/c space group, with unit cell parameters of a=15.7298(4) Å, b=19.9360(6) Å, c=8.4652(3) Å, α=90°, β=101.262(3)°, γ=90°, V=2603.47(12) Å3. FIG. 15 is a schematic diagram of an asymmetric structural unit of the crystal, and the asymmetric unit contains 1 cation of the compound shown in formula I, 2 chloride ions and 2 crystal waters.

Instruments, Software and Methods Used in the Experiment

X-Ray Powder Diffraction (XRPD)

The solid samples obtained in the experiment were analyzed by X-ray powder diffractometer Bruker D8 Advance (Bruker, GER). The 2θ scan angle was from 3° to 45°, the scan step was 0.02°, and the exposure time was 0.12 s. When testing the sample, the voltage and current of the light tube were 40 kV and 40 mA, respectively, and the sample tray was a zero-background sample tray.

Single Crystal X-Ray Diffraction (SCXRD)

A single crystal with a suitable shape and size was selected from the cultured single crystal sample, and the single crystal was sticked to a Loop ring, and then the single crystal sample was placed on a crystal carrier stage. The pre-experiment of single crystal samples and the collection of single crystal diffraction data were carried out using SuperNova (Rigaku, JPN) single crystal diffractometer (Cu target light source, λ=1.54184 Å) at a temperature of 253.0 K, and the diffraction data were analyzed and processed using CrysAlisPro software package.

The angle range of diffraction data collection at the temperature of 253.0 K was 4.4340°<θ<73.8890°, and 8128 diffraction points were collected from this angle range, which were analyzed by CrysAlisPro program and refined by least square method to obtain the unit cell parameters and orientation matrix of the crystal. The completeness of data collection corresponding to the highest θ angle (θ=66.97°) was 99.94%.

Data Restoration

CrysAlisPro 1.171.39.46 (Rigaku Oxford Diffraction, 2018) program was used to restore and integrate each frame of diffraction images collected by the detector, and a total of 16,159 diffraction points were collected, including 4,275 independent diffraction points. Diffraction data were corrected for absorption using the SCALE3 ABSPACK scaling algorithm. The crystal sample had a linear absorption coefficient of 3.404 $mm^{-1}$ for X-rays with a wavelength of λ=1.54184 Å, a minimum transmission coefficient (Tmin) of 0.586, and a maximum transmission coefficient (Tmax) of 1.000. The intensities of all equivalent diffraction points were substantially equal within the experimental error range, with a Rint of 4.30%.

Structural Analysis and Refinement

OLEX2 software was used for the structural analysis of the single crystal, and the diffraction data were initially solved with XS (Sheldrick, 2008) initial solution program and the space group to which the crystals belonged was determined to be P21/c. Subsequent structural refinement was performed using the XH (Sheldrick, 2008) procedure. The coordinates of all non-hydrogen atoms were determined by several rounds of difference Fourier synthesis, followed by anisotropic refinement of all non-hydrogen atoms by full-matrix least squares. All hydrogen atoms were calculated by theoretical hydrogenation.

Crystal Structure Diagram

The schematic diagram of crystal structure and atomic thermal vibration ellipsoid diagram were drawn by Diamond software.

Although the specific embodiments of the present disclosure have been described above, those skilled in the art should understand that these are only examples, and the protection scope of the present disclosure is defined by the appended claims. Those skilled in the art can make various changes or modifications to these embodiments without departing from the principle and essence of the present disclosure, but these changes and modifications all fall within the protection scope of the present disclosure.

What is claimed is:

1. A crystal form A of a hydrochloride hydrate of a compound shown in formula I, wherein an X-ray powder diffraction pattern thereof has characteristic diffraction peaks at the following 2θ angles: 5.9°±0.2°, 7.4°+0.2°, 11.6°±0.2°, 21.7°+0.2° and 23.8°±0.2°;

I

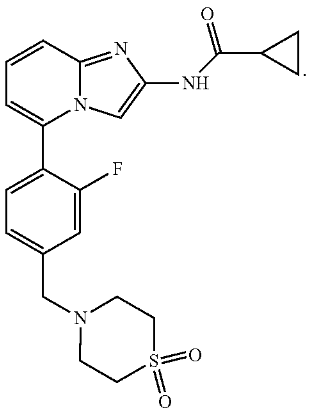

2. The crystal form A of the hydrochloride hydrate of the compound shown in formula I as claimed in claim 1, wherein the X-ray powder diffraction pattern of the crystal form A has characteristic diffraction peaks at the following 2θ angles: 5.9°±0.2°, 7.4°±0.2°, 11.6°±0.2°, 17.7°±0.2°, 17.8°±0.2°, 21.7°±0.2°, 23.6°±0.2°, 23.8°±0.2°, 29.0°±0.2°, 30.4°±0.2° and 34.9°±0.2°.

3. The crystal form A of the hydrochloride hydrate of the compound shown in formula I as claimed in claim 1, wherein the X-ray powder diffraction pattern of the crystal form A has characteristic diffraction peaks at the following 2θ angles: 5.9°±0.2°, 7.4°±0.2°, 8.9°±0.2°, 11.6°±0.2°, 14.6°±0.2°, 17.7°±0.2°, 17.8°±0.2°, 18.7°±0.2°, 19.5°±0.2°, 21.0°±0.2°, 21.7°±0.2°, 21.9°±0.2°, 22.6°±0.2°, 23.6°±0.2°, 23.8°±0.2°, 29.0°±0.2°, 30.4°±0.2°, 33.3°±0.2°, 34.9°±0.2° and 37.7°±0.2°.

4. The crystal form A of the hydrochloride hydrate of the compound shown in formula I as claimed in claim 1, wherein XRPD pattern analytical data of the crystal form A are as shown in Table 1 and FIG. 1.

5. The crystal form A of the hydrochloride hydrate of the compound shown in formula I as claimed in claim 1, wherein the crystal form A of the hydrochloride hydrate of the compound shown in formula I meets one or more of the following conditions:

(1) a thermogravimetric analysis curve of the crystal form A has a weight loss of 8.31±0.50% before 148° C.; and a weight loss of 4.76±0.50% at 148° C. to 228° C.;

(2) a differential scanning calorimetry analysis pattern of the crystal form A has absorption peaks at 165° C.±3° C. and 198° C.±3° C., respectively;

(3) a differential scanning calorimetry analysis pattern of the crystal form A has absorption peaks with initial temperatures of 141° C.±3° C. and 179° C.±3° C., respectively.

6. The crystal form A of the hydrochloride hydrate of the compound shown in formula I as claimed in claim 1, wherein the crystal form A is a single crystal, which belongs to a monoclinic crystal system, P21/c space group, with unit cell parameters of a=15.7298(4) Å, b=19.9360(6) Å, c=8.4652(3) Å, α=90°, β=101.262 (3)°, γ=90°, and a unit cell volume of V=2603.47(12) Å3.

7. The crystal form A of the hydrochloride hydrate of the compound shown in formula I as claimed in claim 1, wherein in the crystal form A, the compound shown in formula I, HCl and water have a molar ratio of 1:x:y, wherein x is greater than 0 but not greater than 3, and y is greater than 0 but not greater than 3.

8. A preparation method for the crystal form A of the hydrochloride hydrate of the compound shown in formula I as claimed in claim 1, wherein the method comprises the following steps: precipitating a crystal from a hydrochloride solution of the compound shown in formula I, the crystal being crystal form A; wherein the hydrochloride solution of the compound shown in formula I contains hydrochloride of the compound shown in formula I, an organic solvent and water, and the organic solvent is one or a mixture of two or more selected from methanol, ethanol, n-propanol, n-butanol, isopropanol, isobutanol and tert-butanol.

9. The preparation method for the crystal form A of the hydrochloride hydrate of the compound shown in formula I as claimed in claim 8, wherein in the hydrochloride of the compound shown in formula I, the compound shown in formula I and HCl have a molar ratio of 1:x, x being greater than 0 but not greater than 3;

or, the organic solvent and water have a volume ratio of 10:1 to 6:1;

or, the hydrochloride solution of the compound shown in formula I has a temperature of 30 to 70° C.;

or, the step of precipitating the crystal from the hydrochloride solution of the compound shown in formula I comprises: cooling the hydrochloride solution of the compound shown in formula I;

or, the step of precipitating the crystal from the hydrochloride solution of the compound shown in formula I comprises: stirring the hydrochloride solution of the compound shown in formula I at 20° C. to 30° C. to precipitate the crystal;

or, the preparation method further comprises: after precipitating the crystal from the hydrochloride solution of the compound shown in formula I, filtering, washing and drying the resulting filter cake to obtain crystal form A;

or, the preparation method further comprises: cooling a solution of the crystal form A of the hydrochloride hydrate of the compound shown in formula I for crystallization to obtain a single crystal of the crystal form A of the hydrochloride hydrate of the compound shown in formula I, wherein the solvent of the solution of the crystal form A of the hydrochloride hydrate of the compound shown in formula I is a mixture of ethanol and water.

10. The preparation method for the crystal form A of the hydrochloride hydrate of the compound shown in formula I as claimed in claim 8, wherein the hydrochloride solution of the compound shown in formula I is obtained by mixing a raw material comprising the hydrochloride hydrate of the compound shown in formula I, the organic solvent and water;

or, the hydrochloride solution of the compound shown in formula I is obtained by mixing a raw material comprising the compound shown in formula I, the organic solvent, water and a concentrated hydrochloric acid solution;

or, wherein the hydrochloride solution of the compound shown in formula I is obtained by mixing a raw material comprising a solution of the compound shown in formula I and a concentrated hydrochloric acid solution.

11. The preparation method for the crystal form A of the hydrochloride hydrate of the compound shown in formula I as claimed in claim 10, wherein the concentrated hydrochloric acid solution and the compound shown in formula I have a ratio of 0.38 mL-0.57 mL:1 g;

or, the organic solvent and the compound shown in formula I have a ratio of 5 mL-15 mL:1 g;

or, the concentrated hydrochloric acid solution has a concentration of 8 mol/L-12 mol/L.

12. A hydrochloride hydrate of a compound shown in formula I, wherein in the hydrochloride hydrate, the compound shown in formula I, HCl and water have a molar ratio of 1:x:y, x being greater than 0 but not greater than 3, and y being greater than 0 but not greater than 3;

I

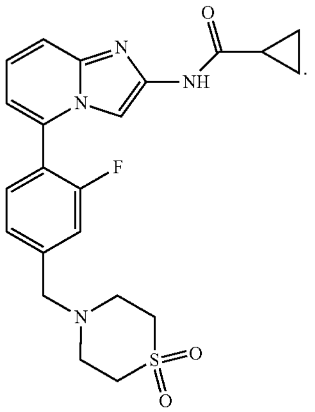

13. A pharmaceutical composition comprising the crystal form A of the hydrochloride hydrate of the compound shown in formula I as claimed in claim 1, and at least one pharmaceutically acceptable carrier.

14. A method for inhibiting a Janus kinase in a subject in need thereof, comprising: administering an effective amount of the crystal form A of the hydrochloride hydrate of the compound shown in formula I as claimed in claim 1 to the subject.

15. A method for treating at least one of hyperproliferative disease, cancer, immune conditions and inflammatory conditions in a subject in need thereof, comprising: administering an effective amount of the crystal form A of the hydrochloride hydrate of the compound shown in formula I as claimed in claim 1 to the subject.

16. A method for treating at least one of immune conditions and inflammatory conditions in a subject in need thereof, comprising: administering an effective amount of the crystal form A of the hydrochloride hydrate of the compound shown in formula I as claimed in claim 1 to the subject.

17. A method for treating at least one of leukemia, lymphoma, transplant rejection, asthma, chronic obstructive pulmonary disease, allergy, rheumatoid arthritis, psoriasis, atopic dermatitis, Crohn's disease, ulcerative colitis, amyotrophic lateral sclerosis and multiple sclerosis in a subject in need thereof, comprising: administering an effective amount of the crystal form A of the hydrochloride hydrate of the compound shown in formula I as claimed in claim 1 to the subject.

18. A method for treating at least one of transplant rejection, asthma, chronic obstructive pulmonary disease, allergy, rheumatoid arthritis, psoriasis, atopic dermatitis, Crohn's disease, ulcerative colitis, amyotrophic lateral sclerosis and multiple sclerosis in a subject in need thereof, comprising: administering an effective amount of the crystal form A of the hydrochloride hydrate of the compound shown in formula I as claimed in claim 1 to the subject.

19. A method for treating at least one of transplant rejection, rheumatoid arthritis, atopic dermatitis, Crohn's disease and ulcerative colitis in a subject in need thereof, comprising: administering an effective amount of the crystal form A of the hydrochloride hydrate of the compound shown in formula I as claimed in claim 1 to the subject.

20. A method for treating rheumatoid arthritis in a subject in need thereof, comprising: administering an effective amount of the crystal form A of the hydrochloride hydrate of the compound shown in formula I as claimed in claim 1 to the subject.

* * * * *